US010188965B2

(12) United States Patent
Pham et al.

(10) Patent No.: US 10,188,965 B2
(45) Date of Patent: Jan. 29, 2019

(54) HYDROPHOBIC CHARGE INDUCTION CHROMATOGRAPHIC DEPLETION OF A PROTEIN FROM A SOLUTION

(71) Applicant: CSL LIMITED, Parkville, Victoria (AU)

(72) Inventors: Hung Pham, Coburg (AU); Jeffrey Michael Hey, Hurstbridge (AU); Darren Nguy, Derrimut (AU)

(73) Assignee: CSL BEHRING GMBH, Marburg (DE)

( * ) Notice: Subject to any disclaimer, the term of this patent is extended or adjusted under 35 U.S.C. 154(b) by 0 days.

(21) Appl. No.: 14/649,374

(22) PCT Filed: Dec. 5, 2013

(86) PCT No.: PCT/AU2013/001414
§ 371 (c)(1),
(2) Date: Jun. 3, 2015

(87) PCT Pub. No.: WO2014/085861
PCT Pub. Date: Jun. 12, 2014

(65) Prior Publication Data
US 2015/0366947 A1  Dec. 24, 2015

Related U.S. Application Data

(63) Continuation-in-part of application No. 13/803,740, filed on Mar. 14, 2013, now abandoned.

(60) Provisional application No. 61/733,761, filed on Dec. 5, 2012.

(30) Foreign Application Priority Data

Feb. 4, 2013 (EP) .................................... 13153898
Apr. 10, 2013 (AU) ............................... 2013203357

(51) Int. Cl.
| C07K 14/75 | (2006.01) |
| B01D 15/36 | (2006.01) |
| A61J 1/05 | (2006.01) |
| C07K 14/745 | (2006.01) |
| C07K 14/755 | (2006.01) |
| A61K 38/00 | (2006.01) |

(52) U.S. Cl.
CPC .............. *B01D 15/363* (2013.01); *A61J 1/05* (2013.01); *C07K 14/745* (2013.01); *C07K 14/75* (2013.01); *C07K 14/755* (2013.01); *A61K 38/00* (2013.01)

(58) Field of Classification Search
CPC .... B01D 15/363; C07K 14/745; C07K 14/75; A61K 38/00
USPC ......................................................... 530/382
See application file for complete search history.

(56) References Cited

U.S. PATENT DOCUMENTS

| 4,540,573 A | 9/1985 | Neurath et al. |
| 4,764,369 A | 8/1988 | Neurath et al. |
| 6,037,457 A | 3/2000 | Lord |
| 6,960,463 B2 | 11/2005 | Kanellos et al. |
| 6,967,239 B1 | 11/2005 | Chtourou et al. |
| 7,045,601 B2 | 5/2006 | Metzner et al. |
| 7,144,487 B2 | 12/2006 | Seabrook et al. |
| 7,211,650 B2 | 5/2007 | McCreath et al. |
| 7,442,308 B2 | 10/2008 | Ristol Debart et al. |
| 7,550,567 B2 | 6/2009 | Metzner et al. |

(Continued)

FOREIGN PATENT DOCUMENTS

| CA | 2 785 594 A1 | 7/2011 |
| EP | 0 555 135 A1 | 6/1993 |

(Continued)

OTHER PUBLICATIONS

Sawyerr et al. Serum Concentrations of Von Willebrand Factor and Soluble Thrombomodulin Indicate Alteration of Endothelial Function in Inflammatory Bowel Diseases; Digestive Diseases and Sciences, vol. 40, No. 4 (1995) pp. 793-799.*

(Continued)

*Primary Examiner* — Scott Long
*Assistant Examiner* — Paul C Martin
(74) *Attorney, Agent, or Firm* — Finnegan, Henderson, Farabow, Garrett & Dunner, L.L.P.

(57) ABSTRACT

The present invention relates generally to a method of reducing the level of at least one protein selected from the group consisting of plasminogen, tissue plasminogen activator and other protease(s) in a solution comprising at least one protein selected from the group consisting of fibrinogen, Factor VIII and von Willebrand factor (VWF), the method comprising: (i) passing a feedstock comprising at least one protein selected from the group consisting of fibrinogen, Factor VIII and VWF through a hydrophobic charge-induction chromatographic resin under conditions selected such that at least one protein selected from the group consisting of plasminogen, tissue plasminogen activator and other protease(s) present in the feedstock is bound to the resin; and (ii) recovering a solution comprising the at least one protein selected from the group consisting of fibrinogen, Factor VIII and VWF which passes through the resin, wherein the concentration of the at least one protein selected from the group consisting of plasminogen, tissue plasminogen activator and other protease(s) in the solution is reduced by at least 50% compared to the feedstock. Also provided are solutions and pharmaceutical formulations comprising the fibrinogen and/or Factor VIII and/or VWF recovered by such methods, and uses thereof.

10 Claims, 10 Drawing Sheets

(56) References Cited

U.S. PATENT DOCUMENTS

| | | | |
|---|---|---|---|
| 7,625,866 | B2 | 12/2009 | Kumpe et al. |
| 7,919,592 | B2 | 4/2011 | Lengsfeld et al. |
| 8,329,871 | B2 | 12/2012 | Borgvall et al. |
| 2005/0197493 | A1 | 9/2005 | Metzner et al. |
| 2010/0204452 | A1 | 8/2010 | Bang et al. |
| 2011/0034672 | A1 | 2/2011 | Falkenstein et al. |
| 2012/0149878 | A1 | 6/2012 | Gillespie et al. |
| 2014/0154233 | A1 | 6/2014 | Pham et al. |

FOREIGN PATENT DOCUMENTS

| | | |
|---|---|---|
| EP | 1 240 200 B1 | 6/2009 |
| EP | 1 519 944 B1 | 11/2009 |
| JP | H03-501974 A | 5/1991 |
| JP | H10-506607 A | 6/1998 |
| JP | 2005-524092 A | 8/2005 |
| JP | 2010-536832 A | 12/2010 |
| WO | WO 89/12065 A1 | 12/1989 |
| WO | WO 93/05067 A1 | 3/1993 |
| WO | WO 96/02571 A1 | 2/1996 |
| WO | WO 01/48016 A1 | 7/2001 |
| WO | WO 03/037914 A2 | 5/2003 |
| WO | WO 03/102132 A2 | 12/2003 |
| WO | WO 2006/007429 A1 | 1/2006 |
| WO | WO 2008/081025 A1 | 7/2008 |
| WO | WO 2009/024620 A2 | 2/2009 |
| WO | WO 2011/083153 A2 | 7/2011 |
| WO | WO 2012/038410 A1 | 3/2012 |
| WO | WO 2013/135684 A1 | 9/2013 |

OTHER PUBLICATIONS

2008 Pall Life Scienes AcroSep™ HEA and PPA Hypercel™ Columns prouct sheets: 16 pages total.

Arakawa et al. "The Effects of Arginine on Protein Binding and Elution in Hydrophobic Interaction and Ion-Exchange Chromatography," Protein Expression and Purification, vol. 54 (2007) pp. 110-116 (7 pages).

S.C. Burton et al., "Hydrophobic charge induction chromatography: salt independent protein adsorption and facile elution with aqueous buffers," J. Chromatography A, 814:71-81 (1998).

B. Cardinali et al., "Hydrodynamic and mass spectrometry analysis of nearly-intact human fibrinogen, chicken fibrinogen, and of a substantially monodisperse human fibrinogen fragment X," Archives Biochem, Biophys, 493:157-168 (2010).

A. Clauss, "Gerinnungsphysiologische Schnellmethode zur Bestimmung des Fibrinogens," Acta haemat., 17:237-246 (1957).

E. J. Cohn et al.; "Preparation and Properties of Serum and Plasma Proteins, IV. A System for the Separation into Fractions of the Protein and Lipoprotein Components of Biological Tissues and Fluids," J. Am. Chem. Soc., 68(3):459-475 (1946).

Delahunty et al. "Relationship Between Serum PH and Seizure Onset Following Birth Asphyxia in the Newborn," Proceedings of the Physiological Society, vol. 23 (2011) Poster Communication 23 (1 page).

K. Jacobsson et al., "I. Studies on the Determination of Fibrinogen in Human Blood Plasma, II. Studies on the Trypsin and Plasmin Inhibitors in Human Blood Serum," Scandinavian J. Clin. Lab, Invest., 7(Supp. 14), 51 pages (1955).

Keeling et al. "Crypoprecipitate Prepared From Plasma Virally Inactivated by the Solvent Detergent Method." British Journal of Haematology, vol. 96 (1997) pp. 194-197 (4 pages).

M. P. Kosloski et al., "Role of Glycosylation in Conformational Stability, Activity, Macromolecular Interaction and Immunogenicity of Recombinant Human Factor VIII," AAPS J., 11(3):424-431 (2009).

Li et al. "The Use of a Bulk Protein Depletion Strategy Improves the Performance of Troponin 1 Elisa," Pall Life Sciences (2009) downloaded from www.pall.com_pdfs_OEM-Materials-and-Devices_09.2960_AACC_Tech_Poster1.pdf on Apr. 6, 2015 (1 page).

I. J. Mackie et al., "Guideline: Guidelines on Fibrinogen Assays," Br. J. Haematol., 121:396-404 (2003).

"Monograph 903-Fibrin Sealant Kit: Fibrini glutinum," European Pharmacopoeia 7.0, pp. 2014-2015 (2012).

Pall Corporation, Hydrophobic Charge Interaction Chromatography webpage, <http://www.pall.com/main/laboratory/hydrophobic-charge-interaction-chromatog-52127.page>, accessed Oct. 22, 2014 (2 pages).

Pezzini et al. "Rapid Screening of Purification Strategies for the Capture of a Human Recombinant F(ab')2 Expressed in Baculovirus-Infected Cells Using a Micro-Plate Approach and Seldi-MS," Journal of Chromatography B, vol. 877 (2009) pp. 2428-2434 (7 pages).

Qiu et al. "Convenient and Effective Method for Removing Fibrinogen From Serum Specimens Before Protein Electrophoresis," Clinical Chemistry, vol. 49, No. 6 (2003) pp. 868-872 (5 pages).

"Tisseel Ready to Use (Calcium chloride, Aprotinin, Human fibrinogen Human thrombin), PL 00116/0627," Medicines and Healthcare Products Regutatory Agency, retrieved on Feb. 25, 2014.

M. Vuento et al., "Purification of Fibronectin from Human Plasma by Affinity Chromatography under Non-Denaturing Conditions," Biochem. J., 183:331-337 (1979).

Welker et al. "Aluminum Hydroxide as a Protein Precipitating Reagent in the Determination of Lactose in Milk," Journal of the American Chemical Society, vol. 35, No. 6 (1913) pp. 823-824 (2 pages).

Extended European Search Report for European Patent App. No. 13153898.5, dated Jun. 19, 2013 (8 pages).

Office Action dated Mar. 2, 2015, in U.S. Appl. No. 14/535,085 (20 pages).

Office Action dated Apr. 10, 2015, in U.S. Appl. No. 13/803,740 (22 pages).

Office Action dated Aug. 11, 2014, in U.S. Appl. No. 13/803,740 (16 pages).

Office Action dated Dec. 27, 2013, in U.S. Appl. No. 13/803,740 (23 pages).

Office Action dated May 2, 2014, in U.S. Appl. No. 13/803,740 (17 pages).

Office Action dated Nov. 4, 2013, in U.S. Appl. No. 13/803,740 (9 pages).

PCT Notification of Transmittal of The International Search Report and The Written Opinion of the International Searching Authority, issued in International Application No. PCT/AU2013/001414, dated Feb. 27, 2014 (14 pages).

Cooper, A. et al., "Fibrinogen gamma-chain splice variant Y' alters fibrin formation and structure," Blood, 102(2):535-40, (2003).

Jennissen, H.P. et al., "Interaction of fibrinogen with n-alkylagaroses and its purification by critical hydrophobicity hydrophobic interaction chromatography," J. Chrom. A, 1109:197-213, (2006).

Spadiut, O., et al., "Purification of a recombinant plant peroxidase produced in *Pichia pastoris* by a simple 2-step strategy," *Protein Expression and Purification*, Sep. 28, 2012, vol. 86, No. 2, pp. 89-97.

Rozenfeld M.A. et al., "Mechanism of Enzymatic Crosslinking of Fibrinogen Molecules," Izvestiya Rossiyskoy akademii nauk. Seriya biologicheskaya, 6:671-679 (2008).

Vladimirov, Yu, et al., "Calcium Pumps of a Living Cell," Sorosovskiy obrazovatelniy zhurnal, 4(3):20-27 (1998).

Zhao, G. et al., "Ligands for Mixed-Mode Protein Chromatography: Principles, Characteristics and Design," Journal of Biotechnology, 144:3-11 (2009).

\* cited by examiner

HYDROPHOBIC CHARGE INDUCTION CHROMATOGRAPHIC DEPLETION OF A PROTEIN FROM A SOLUTION

CROSS REFERENCE TO RELATED APPLICATIONS

This application is a national phase application based on International Application No. PCT/AU2013/001414, filed Dec. 5, 2013, which claims priority of European Patent Application No. 13153898.5, filed Feb. 4, 2013, and Australian Patent Application No. 20132013357, filed Apr. 10, 2013, and is a continuation-in-part of U.S. application Ser. No. 13/803,740, filed Mar. 14, 2013, and claims the benefit of U.S. Provisional Application No. 61/733,761, filed Dec. 5, 2012, and the contents of all of which are incorporated herein by reference.

TECHNICAL FIELD

The present invention relates generally to a method of reducing the level of impurities in a solution containing at least one therapeutic protein and to the resultant therapeutic-protein containing solutions. More specifically, to a method of reducing the level of plasminogen and/or tissue plasminogen activator and/or other protease(s) in a feedstock comprising fibrinogen and/or Factor VIII and/or Von Willebrand factor (VWF). The present invention also relates generally to solutions and pharmaceutical formulations comprising the fibrinogen and/or Factor VIII and/or VWF recovered by such methods, and uses thereof.

BACKGROUND

Current methods of purifying a naturally-occurring or recombinant therapeutic protein from a solution comprising said protein usually carry at least some impurities into the final preparation. In some instances, the presence of impurities, such as proteases, will destabilise the therapeutic protein in solution, particularly during storage. For this reason, many therapeutic proteins are stored as lyophilized or frozen preparations.

Whilst destabilising levels of impurities can affect many different types of therapeutic proteins, they are particularly relevant to those used for maintaining haemostasis. Haemostasis is an important physiological process that prevents bleeding following damage (e.g. a rupture) to blood vessels. There are three basic mechanisms that promote haemostasis: (i) vasoconstriction, (ii) platelet aggregation at the rupture site; and (iii) coagulation. During coagulation, damaged endothelial cells release tissue factor (Factor III), which in turn activates Factor VII with the aid of $Ca^{2+}$. Factor XII, which is released by activated platelets, activates Factor XI. Activated Factor VII and Factor XI promote a cascade of enzymatic reactions that lead to the activation of Factor X. Active Factor X (Factor Xa), along with Factor III, Factor V, $Ca^{2+}$, and platelet thromboplastic factor ($PF_3$), activate prothrombin activator. Prothrombin activator converts prothrombin to thrombin, which converts fibrinogen (Factor I) to fibrin, which forms an initial mesh over the site of damage. The initial mesh is then converted to a dense fibrin clot by Factor XIII, sealing the rupture until the site is repaired. During the coagulation cascade, thrombin will also activate Factor VIII, a glycoprotein pro-cofactor that in the circulation is mainly complexed to von Willebrand factor (VWF). Factor VIII interacts with Factor IXa to activate Factor X in the presence of $Ca^{+2}$ and phospholipids.

A deficiency in the level of any one or more of the proteins involved in coagulation, including fibrinogen, Factor VIII, and/or von Willebrand factor (VWF) whether congenital or acquired, can lead to insufficient clotting of blood and the risk of haemorrhage. Current treatment options are limited to the administration of a pharmaceutical preparation of one or more therapeutic proteins, with a view to restoring endogenous levels of said proteins and maintaining haemostasis. However, existing pharmaceutical preparations, which are typically derived from donated blood plasma or a recombinant source, comprise zymogens and proteases (e.g., prothrombin, plasminogen, tissue plasminogen activator (tPA) and/or other proteases), which can destabilise the therapeutic proteins, such as fibrinogen, Factor VIII, or VWF during storage. As a consequence, such preparations are relatively unstable in aqueous solution, with long-term storage limited to lyophilized or frozen preparations.

For clinical applications, fibrinogen is typically purified from human plasma, where it accounts for only about 2-5% (1.5-4.0 g/L) of total plasma proteins. Traditionally, the purification of fibrinogen from plasma is carried out by classical plasma fractionation, where fibrinogen is cryo-precipitated from plasma followed by precipitation with either ethanol, ammonium sulphate, β alanine/glycine, polymers (e.g., polyethelene glycol) or low ionic strength solutions. Such methods can achieve relative high yield and homogeneity. Where a greater level of purity is required, chromatographic techniques are often employed. However, existing precipitation and chromatographic techniques amenable to commercial scale manufacturing processes typically produce fibrinogen preparations that comprise contaminating proteins such as zymogens or proteases (e.g., prothrombin, tissue plasminogen activator (tPA) and plasminogen), which can destabilize fibrinogen in solution. For example, when prothrombin is present, it can be activated to the serine protease thrombin which will in turn convert fibrinogen into fibrin. Similarly, when both tPA and plasminogen are present, tPA can activate plasminogen to its active form plasmin, which will in turn hydrolyse fibrinogen into fibrin. As a consequence, fibrinogen preparations are relatively unstable in aqueous solution, with long-term storage limited to lyophilized or frozen preparations.

Specific contaminants can be absorbed out; for example, fibronectin on immobilised gelatine and plasminogen on immobilised lysine (Vuento et al. 1979, Biochem. J., 183 (2):331-337). However, the use of specific affinity resins is not amenable to large scale commercial processes. Reasons for this include the affinity resins themselves not being sufficiently robust to be used repeatedly and generally add significantly to the both processing time and costs.

EP1240200 (U.S. Pat. No. 6,960,463) is directed to methods of purifying fibrinogen from a fibrinogen-containing solution using ion exchange (IEX) chromatography. In particular the method involves applying a fibrinogen-containing solution to an ion exchange matrix under conditions that allow the fibrinogen to bind to the matrix and then washing the ion exchange matrix with a solution comprising at least one omega amino acid. This is done to promote the differential removal of plasminogen from the resin. Fibrinogen that is bound to the matrix is then eluted from the matrix.

WO2012038410 provides a method of purifying fibrinogen using anion exchange resins which contain a hydroxylated polymer support grafted with tertiary or quaternary amines that bind fibrinogen.

EP519944 teaches the use of an immobilized metal ion affinity chromatography matrix under conditions that fibrinogen and plasminogen bind to the matrix, and selectively eluting the fibrinogen and plasminogen separately, such that the main fibrinogen fraction contains about 600 ng of plasminogen per mg of protein.

The present invention provides a method of reducing the level of plasminogen and/or tissue plasminogen activator and/or other protease(s) in a solution comprising fibrinogen and/or Factor VIII and/or VWF. The purified protein(s) are stable during storage as liquid preparations and can be used for clinical or veterinary applications, including treating or preventing conditions associated with a deficiency in the level of said protein(s).

SUMMARY OF THE INVENTION

In an aspect of the present invention, there is provided a method of reducing the level of at least one protein selected from the group consisting of plasminogen, tissue plasminogen activator and other protease(s) in a solution comprising at least one protein selected from the group consisting of fibrinogen, Factor VIII and von Willebrand factor (VWF), the method comprising:
  (i) passing a feedstock comprising at least one protein selected from the group consisting of fibrinogen, Factor VIII and VWF through a hydrophobic charge-induction chromatographic resin under conditions selected such that at least one protein selected from the group consisting of plasminogen, tissue plasminogen activator and other protease(s) present in the feedstock is bound to the resin; and
  (ii) recovering a solution comprising the at least one protein selected from the group consisting of fibrinogen, Factor VIII and VWF which passes through the resin, wherein the concentration of the at least one protein selected from the group consisting of plasminogen, tissue plasminogen activator and other protease(s) in the solution is reduced by at least 50% compared to the feedstock.

In another aspect of the present invention, there is provided a method of reducing the level of at least one protein selected from the group consisting of plasminogen, tissue plasminogen activator and other protease(s) in a solution comprising at least one protein selected from the group consisting of fibrinogen, Factor VIII and von Willebrand factor (VWF), the method comprising:
  (i) passing a feedstock comprising at least one protein selected from the group consisting of fibrinogen, Factor VIII and VWF through a first hydrophobic charge-induction chromatographic resin;
  (ii) recovering a solution comprising the at least one protein selected from the group consisting of fibrinogen, Factor VIII and VWF which passes through the first hydrophobic charge-induction chromatographic resin;
  (iii) passing the solution that is recovered in step (ii) through a second hydrophobic charge-induction chromatographic resin; and
  (iv) recovering the solution comprising the at least one protein selected from the group consisting of fibrinogen, Factor VIII and VWF which passes through the second hydrophobic charge-induction chromatographic resin;
wherein the conditions of the chromatographic steps are such that at least one protein selected from the group consisting of plasminogen, tissue plasminogen activator and other protease(s) present in the feedstock is bound to the first and/or second resin, and wherein the concentration of the at least one protein selected from the group consisting of plasminogen, tissue plasminogen activator and other protease(s) in the solution that is recovered in step (iv) is reduced by at least 50% compared to the feedstock.

In another aspect, there is provided a solution comprising at least one protein selected from the group consisting of fibrinogen, Factor VIII and VWF recovered by the method of the present invention as herein described.

In another aspect, there is provided a vessel containing at least 5 mL of a stable pharmaceutically acceptable fibrinogen solution, wherein the concentration of fibrinogen is at least 20 mg/mL.

In another aspect, there is provided a pharmaceutical formulation comprising a solution comprising at least one protein selected from the group consisting of fibrinogen, Factor VIII and VWF recovered by the method of the present invention, as herein described, and a pharmaceutically acceptable carrier.

In another aspect of the present invention, there is provided a solution comprising:
  (a) at least 75% total protein of fibrinogen;
  (b) less than 50 pg/mg total protein of tissue plasminogen activator, and/or
  (c) less than 1 g/mg total protein of plasminogen.

In another aspect of the present invention, there is provided a solution comprising:
  (a) at least 90% total protein of fibrinogen;
  (b) less than 50 pg/mg total protein of tissue plasminogen activator; and/or
  (c) less than 150 ng/mg total protein of plasminogen.

In another aspect of the present invention, there is provided a solution comprising:
  (a) at least 90% total protein of fibrinogen;
  (b) less than 20 pg/mg total protein of tissue plasminogen activator; and/or
  (c) less than 10 ng/mg total protein of plasminogen.

In another aspect, there is provided a method of treating or preventing a condition associated with fibrinogen deficiency, the method comprising administering to a subject in need thereof the solution or pharmaceutical formulation of the present invention, as herein described.

In another aspect, there is provided use of the solution of the present invention, as herein described, in the manufacture of a medicament for treating or preventing a condition associated with fibrinogen deficiency.

In another aspect, there is provided a fibrin glue comprising the solution of the present invention, as herein described.

In another aspect, there is provided a method of producing a stable liquid fibrinogen solution, the method comprising:
  (i) passing a feedstock comprising fibrinogen through a hydrophobic charge-induction chromatographic resin under conditions selected such that at least one protein selected from the group consisting of plasminogen, tissue plasminogen activator and other protease(s) present in the feedstock is bound to the resin; and
  (ii) recovering a solution comprising fibrinogen which passes through the resin,
wherein the concentration of the at least one protein selected from the group consisting of plasminogen, tissue plasminogen activator and other protease(s) in the solution is reduced by at least 50% compared to the feedstock.

In another aspect, there is provided a method of producing a stable liquid fibrinogen solution, the method comprising:
  (i) passing a feedstock comprising fibrinogen through a first hydrophobic charge-induction chromatographic resin;

(ii) recovering a solution comprising fibrinogen which passes through the first hydrophobic charge-induction chromatographic resin;

(iii) passing the solution that is recovered in step (ii) through a second hydrophobic charge-induction chromatographic resin; and (iv) recovering a solution comprising fibrinogen which passes through the second hydrophobic charge-induction chromatographic resin;

wherein the conditions of the chromatographic steps are such that at least one protein selected from the group consisting of plasminogen, tissue plasminogen activator and other protease(s) present in the feedstock is bound to the first and/or second resin, and wherein the concentration of the at least one protein selected from the group consisting of plasminogen, tissue plasminogen activator and other protease(s) in the solution that is recovered in step (iv) is reduced by at least 50% compared to the feedstock.

In another aspect of the present invention, there is provided a method for purifying fibrinogen, the method comprising the steps of:

(i) passing a solution comprising fibrinogen through an ion exchange chromatographic resin under conditions selected such that fibrinogen monomer is bound to the resin;

(ii) eluting the fibrinogen monomer from the resin with an elution buffer, and (iii) filtering the eluted fibrinogen monomer from step (ii) through a filter having a pore size in the range from about 15 nm to about 35 nm.

DETAILED DESCRIPTION

Figure 1:
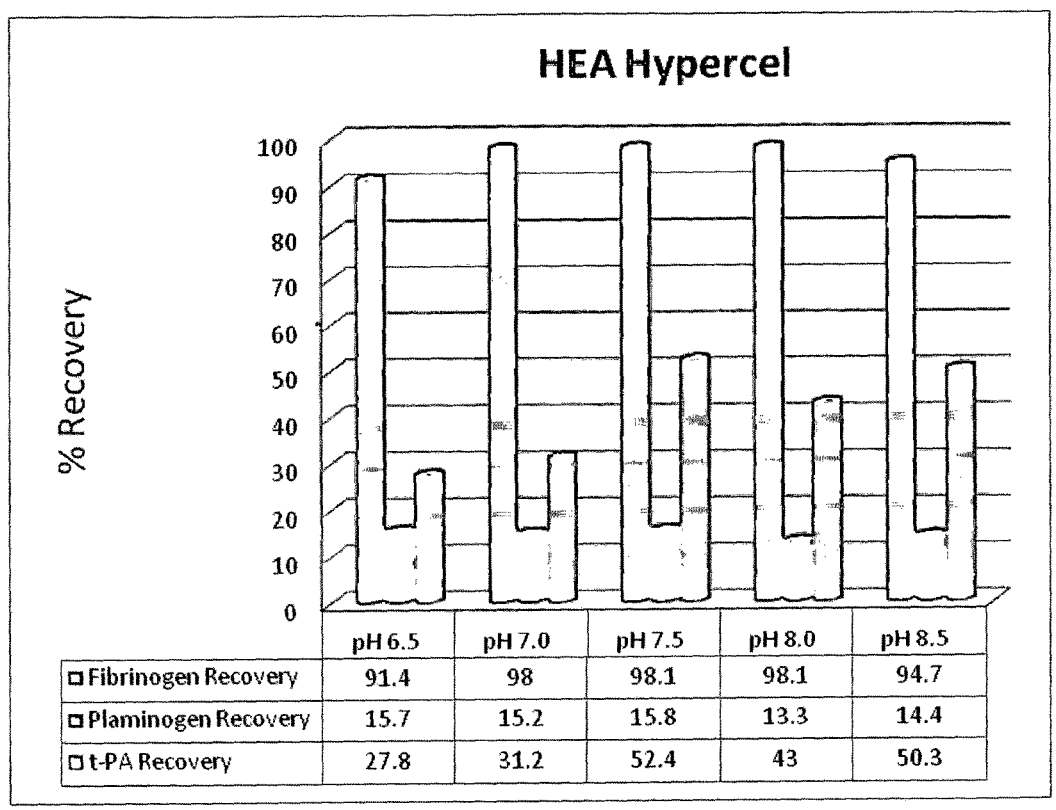
FIG. 1 shows the percentage recovery of fibrinogen, plasminogen and t-PA from a fibrinogen solution over a range of pH levels when the solution is passed through a HEA Hypercel™ in negative mode with respect to fibrinogen. The bars within each group represent (from left to right): Fibrinogen Recovery, Plasminogen Recovery and t-PA Recovery.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a formulation" includes a single formulation, as well as two or more formulations.

In the absence of any indication to the contrary, reference made to a "%" content throughout this specification is to be taken as meaning % w/w (weight/weight). For example, a solution comprising at least 80% total protein of fibrinogen is taken to mean a solution comprising fibrinogen at a concentration of at least 80% w/w of total protein. This can be calculated for example by dividing the amount of fibrinogen derived from the clottable protein assay by the total protein amount derived from a standard protein assay (e.g. Biuret) and multiplying by 100. In the clottable protein assay, thrombin is added to a sample to form a clot, which is almost all fibrin. The clot can be separated from the supernatant containing non-clottable proteins by centrifugation. Subsequently the clot is washed and dissolved by alkaline urea or other substances and the protein concentration is determined by spectrophotometry. Since the majority of the clot is fibrin, the protein concentration will be equivalent to the fibrinogen concentration. Hence the amount of clottable protein in a sample is equivalent to the difference between the total protein and the non-clottable protein component of the sample.

The purification of fibrinogen and/or Factor VIII and/or VWF from a feedstock (e.g., plasma or cell culture supernatant) is typically carried out by conventional fractionation, where the fibrinogen and/or Factor VIII and/or VWF is precipitated from the solution using, for example, ethanol, ammonium sulphate, β alanine/glycine, polymers (e.g., polyethylene glycol) and/or low ionic strength solutions. Current plasma purification methods employing different chromatographic steps can achieve relative high yield and homogeneous preparations of a protein of interest. However, these methods typically result in preparations comprising residual amounts of impurities that may not be suitable for formulating a stable liquid preparation for clinical applications. Impurities such as prothrombin, tissue plasminogen activator (tPA) and plasminogen are particularly problematic, as destabilizing levels of these impurities can hydrolyse fibrinogen in aqueous solution, thus rendering the fibrinogen unstable, particularly during manufacture and/or long-term storage.

The present invention is predicated, at least in part, on the finding that passing a feedstock comprising fibrinogen and/or Factor VIII and/or VWF through a hydrophobic charge-induction chromatographic (HCIC) resin and recovering the solution comprising fibrinogen and/or Factor VIII and/or VWF that passes through the resin is an efficient alternative to existing purification processes for reducing the destabilizing level of plasminogen and/or tissue plasminogen activator and/or other protease(s) in the solution.

Thus, in an aspect of the present invention, there is provided a method of reducing the level of at least one protein selected from the group consisting of plasminogen, tissue plasminogen activator and other protease(s) in a solution comprising at least one protein selected from the group consisting of fibrinogen, Factor VIII and von Willebrand factor (VWF), the method comprising:
  (i) passing a feedstock comprising at least one protein selected from the group consisting of fibrinogen, Factor VIII and VWF through a hydrophobic charge-induction chromatographic resin under conditions selected such that at least one protein selected from the group consisting of plasminogen, tissue plasminogen activator and other protease(s) present in the feedstock is bound to the resin; and
  (ii) recovering a solution comprising the at least one protein selected from the group consisting of fibrinogen, Factor VIII and VWF which passes through the resin, wherein the concentration of the at least one protein selected from the group consisting of plasminogen, tissue plasminogen activator and other protease(s) in the solution is reduced by at least 50% compared to the feedstock.

In an embodiment, the concentration of the plasminogen and/or tissue plasminogen activator and/or other protease(s) in the recovered solution comprising fibrinogen and/or Factor VIII and/or VWF is reduced by at least 60%, by at least 70%, by at least 80%, or by at least 90% or by at least 95% or by at least 98% compared to the feedstock.

In another aspect, there is provided a method of producing a stable liquid fibrinogen solution, the method comprising:
  (i) passing a feedstock comprising fibrinogen through a hydrophobic charge-induction chromatographic resin under conditions selected such that at least one protein selected from the group consisting of plasminogen, tissue plasminogen activator and other protease(s) present in the feedstock is bound to the resin; and
  (ii) recovering a solution comprising fibrinogen which passes through the resin,
wherein the concentration of the at least one protein selected from the group consisting of plasminogen, tissue plasminogen activator and other protease(s) in the solution is reduced by at least 50% compared to the feedstock.

In an embodiment, the concentration of the plasminogen and/or tissue plasminogen activator and/or other protease(s) in the recovered solution comprising fibrinogen is reduced by at least 60%, by at least 70%, by at least 80%, or by at least 90% or by at least 95% or by at least 98% compared to the feedstock.

Chromatographic processes typically employ a solid support, also referred to interchangeably herein as a resin or matrix. Suitable solid supports would be familiar to persons skilled in the art. Examples include inorganic carriers, such as glass and silica gel, organic, synthetic or naturally occurring carriers, such as agarose, cellulose, dextran, polyamide, polyacrylamides, vinyl copolymers of bifunctional acrylates, and various hydroxylated monomers, and the like. Commercially available carriers are sold under the names of SEPHADEX™, SEPHAROSE™, HYPERCEL™, CAPTO™, FRACTOGEL™, MACROPREP™, UNOSPHERE™, GIGACAP™, TRISACRYL™, ULTROGEL™, DYNOSPHERES™, MACROSORB™ and XAD™ resins.

The chromatography steps will generally be carried out under non-denaturing conditions and at convenient temperatures in the range of about +10° C. to +30° C., more usually at about ambient temperatures. The chromatographic steps may be performed batch-wise or continuously, as convenient. Any convenient method of separation may be employed, such as column, centrifugation, filtration, decanting, or the like.

Hydrophobic Charge Induction Chromatography (HCIC) which is often also referred to as either mixed mode, or multimodal chromatography, will be familiar to persons skilled in the art. HCIC uses binding moieties attached to a solid support, wherein the binding moieties may have specificity for one or more proteins that, in accordance with the methods of the present invention, represent impurities in the feedstock (e.g., zymogens and proteases such prothrombin, tPA and plasminogen).

Any suitable HCIC resin known to persons skilled in the art can be used. In an embodiment, the HCIC resin comprises a ligand selected from the group consisting of mercaptoethylpyridine (4-mercaptoethylpyridine, e.g., MEP Hypercel™), n-hexylamine (e.g., HEA Hypercel™) and phenylpropylamine (e.g., PPA Hypercel™). In an embodiment, the HCIC resin comprises n-hexylamine.

HCIC ligands such as HEA, MEP and PPA have an advantage in that they permit separation based on the surface hydrophobicity of proteins, but do not require the addition of lyotropic salts often seen in other processes for the purification of fibrinogen using hydrophobic chromatography (e.g., hydrophobic interaction chromatography; HIC). In contrast to traditional hydrophobic interaction chromatography, HCIC is controlled on the basis of pH, rather than salt concentration. HCIC resins also provide high binding capacity and high flow rates, ideal for both laboratory- and industrial-scale purification.

HCIC resins are often packed into columns with bed heights from about 2 cm to about 40 cm. At industrial scale the bed heights are usually at least 10 cm and are typically in the range from about 15 cm to 25 cm. The column diameters of industrial columns can range from 20 cm up to about 1.5 m. Such columns are operated at flow rates in accordance with HCIC resin manufacture instructions with flow rates in the 50-100 cm/hr range typical. The upper flow rate limitation is in part due to HCIC resin pressure constraints. For HEA resin for example the upper operating pressure limit is <3 bar (<300 kPa). Typical dynamic binding capacities (10% breakthrough of a binding protein) for HCIC resins are about 20 to 30 mg of bound protein per mL of resin. For the present invention, this enables relative large amounts of protein to be loaded onto the HCIC column as the abundant proteins like fibrinogen can pass through the column whilst less abundant proteins such as plasminogen and/or tissue plasminogen activator and/or other protease(s) bind to the HCIC resin. This is advantageous for industrial scale manufacture as either smaller sized columns and/or less column cycles are required to process a batch.

The present inventors have also found that the pH of the solution or feedstock comprising fibrinogen and/or Factor VIII and/or VWF that is passed through the HCIC resin in accordance with the methods of the present invention can be adjusted to control the recovery of the fibrinogen and/or Factor VIII and/or VWF and removal of impurities. Thus, in an embodiment disclosed herein, the solution or feedstock comprising fibrinogen and/or Factor VIII and/or VWF that is passed through the HCIC resin has a pH from about 6.0 to about 9.5. In particular embodiments the solution or feedstock comprising fibrinogen and/or Factor VIII and/or VWF is passed through the HCIC resin preferably at a pH of about 4.0, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5 or 10.0. In a particular embodiment, the solution or feedstock comprising fibrinogen and/or Factor VIII and/or VWF that is passed through the HCIC resin has a pH of about 7.0. In particular embodiments, the HCIC resin is equilibrated prior to loading of the solution or feedstock at a pH of about 4.0, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5 or 10.0.

The method of the present invention may also employ the use of more than one additional chromatography step to remove further impurities, if necessary, and thus improve the purity of the final preparation. Additional chromatographic purification steps can be implemented either before or after the purification of fibrinogen and/or Factor VI and/or VWF through the HCIC resin in accordance with the present invention. For example, the solution comprising fibrinogen and/or Factor VIII and/or VWF that is recovered from the HCIC resin in step (ii) can be passed through another chromatographic resin.

The additional chromatographic purification steps may employ another HCIC resin. Thus, in another aspect of the present invention, there is provided a method of reducing the level of at least one protein selected from the group consisting of plasminogen, tissue plasminogen activator and other protease(s) in a solution comprising at least one protein selected from the group consisting of fibrinogen, Factor VIII and von Willebrand factor (VWF), the method comprising:
  (i) passing a feedstock comprising at least one protein selected from the group consisting of fibrinogen, Factor VIII and VWF through a first hydrophobic charge-induction chromatographic resin;
  (ii) recovering a solution comprising the at least one protein selected from the group consisting of fibrinogen, Factor VIII and VWF which passes through the first hydrophobic charge-induction chromatographic resin;
  (iii) passing the solution that is recovered in step (ii) through a second hydrophobic charge-induction chromatographic resin; and
  (iv) recovering the solution comprising the at least one protein selected from the group consisting of fibrinogen, Factor VIII and VWF which passes through the second hydrophobic charge-induction chromatographic resin;
wherein the conditions of the chromatographic steps are such that at least one protein selected from the group consisting of plasminogen, tissue plasminogen activator and other protease(s) present in the feedstock is bound to the first and/or second resin, and wherein the concentration of the at least one protein selected from the group consisting of plasminogen, tissue plasminogen activator and other protease(s) in the solution that is recovered in step (iv) is reduced by at least 50% compared to the feedstock.

In an embodiment, the concentration of the plasminogen and/or tissue plasminogen activator and/or other protease(s) in the solution comprising fibrinogen and/or Factor VIII and/or VWF that is recovered in step (iv) is reduced by at least 60%, by at least 70%, by at least 80%, or by at least 90% or by at least 95% or by at least 98% compared to the feedstock.

In another aspect, there is provided a method of producing a stable liquid fibrinogen solution, the method comprising:
  (i) passing a feedstock comprising fibrinogen through a first hydrophobic charge-induction chromatographic resin;
  (ii) recovering a solution comprising fibrinogen which passes through the first hydrophobic charge-induction chromatographic resin;
  (iii) passing the solution that is recovered in step (ii) through a second hydrophobic charge-induction chromatographic resin; and
  (iv) recovering a solution comprising fibrinogen which passes through the second hydrophobic charge-induction chromatographic resin;
wherein the conditions of the chromatographic steps are such that at least one protein selected from the group consisting of plasminogen, tissue plasminogen activator and other protease(s) present in the feedstock is bound to the first and/or second resin, and wherein the concentration of the at least one protein selected from the group consisting of plasminogen, tissue plasminogen activator and other protease(s) in the solution that is recovered in step (iv) is reduced by at least 50% compared to the feedstock.

In an embodiment, the concentration of the plasminogen and/or tissue plasminogen activator and/or other protease(s) in the solution comprising fibrinogen that is recovered in step (iv) is reduced by at least 60%, by at least 70%, by at least 80%, or by at least 90% or by at least 95% or by at least 98% compared to the feedstock.

In an embodiment disclosed herein, the second HCIC resin is different from the first HCIC resin. In another embodiment disclosed herein, the first and second hydrophobic charge-induction chromatographic resins are the same. Where the solution comprising fibrinogen and/or Factor VIII and/or VWF that is recovered from the HCIC resin in step (ii) is passed through the same HCIC resin, it may be desirable to wash the HCIC resin after step (ii) and prior to passing the recovered solution through the HCIC resin in step (iii) again in order to remove any impurities that may be bound to the resin.

The additional chromatographic resin may also be an anion exchange chromatographic resin. In anion exchange chromatography, negatively charged molecules are attracted to a positively charged solid support. A positively charged solid support can be prepared by any means known to persons skilled in the art and will usually involve the covalent attachment of a negatively charged functional ligand onto a solid support. Suitable negatively charged functional ligands will invariably depend on the molecule to be separated from solution. Examples of suitable anion exchange resins are ones comprising a functional quaternary amine group (Q) and/or a tertiary amine group (DEAE), or a diethylaminopropyl group (ANX). Commercially available anion exchange chromatography matrices include, but are not limited to, DEAE cellulose, POROS™ PI 20, PI 50, HQ 10, HQ 20, HQ 50, D 50 from Applied Biosystems, MONOQ™, MINIQ™, SOURCE™ 15Q and 30Q, Q, DEAE and ANX SEPHAROSE™ Fast Flow, Q SEPHAROSEM™ high Performance, QAE SEPHADEX™ and FAST Q SEPHAROSE™ from GE Healthcare, WP PEI™, WP DEAM™, WP QUAT™ from J. T. Baker, HYDROCELL™ DEAE and HYDROCELL™ QA from Biochrom Labs Inc., UNOSPHEREM Q, MACRO-PREP™ DEAE and MACRO-PREP™ High Q from Biorad, Ceramic HYPERD™ Q, ceramic HYPERD™ DEAE, Q HYPERZ™, TRISACRYL™ and LS™ DEAE, SPHERODEX™ LS DEAE, QMA SPHEROSIL™ LS, QMA SPHEROSIL™ M from Pall Technologies, DOWEX™ Fine Mesh Strong Base Type I and Type II Anion Matrix and DOWEX™ MONOSPHER E 77, weak base anion from Dow Liquid Separations, Matrex CELLUFINE™ A200, A500, Q500, and Q800, from Millipore, FRACTOGEL™ EMD TMAE3 FRACTOGEL™ EMD DEAE and FRACTOGEL™ EMD DMAE from EMD, AMBERLITE™ weak and strong anion exchangers type I and II, DOWEX™ weak and strong anion exchangers type I and II, DIAION™ weak and strong anion exchangers type I and II, DUOLITE™ from Sigma-Aldrich, TSK™ gel Q and DEAE 5PW and 5PW-HR, TOYOPEARL™ SuperQ-650S, 650M and 650C3 QAE—26-550C and 650S, DEAE-65OM and 650C from Tosoh, and QA52™, DE23™, DE32™, DE51™, DE52™, DE53™, EXPRESS-ION™ D and EXPRESS-ION™ Q from Whatman.

If desirable, an anion exchange chromatography membrane can be used instead of an anion exchange chromatography matrix. Commercially available anion exchange membranes include, but are not limited to, SARTOBIND™ Q from Sartorius, MUSTANG™ Q from Pall Technologies and INTERCEPT™ Q membrane from Millipore.

In an embodiment disclosed herein, the anion exchange resin is a strong anion exchange resin. In another embodiment disclosed herein, the strong anion exchange resin comprises a quaternary amine functional ligand (e.g., —N$^+$(CH$_3$)$_3$ as seen, for example, in MACROPREP™-HQ; Bio-Rad Laboratories). In yet another embodiment the anion exchange resin is trimethylamine groups grafted to a hydroxylated methacrylic polymer via a linking group such as GIGACAP™ Q-650M®.

In an embodiment, anion exchange chromatography is performed in positive mode with respect to the fibrinogen and/or Factor VIII and/or VWF. That is, the conditions used are such that, when the solution or feedstock comprising fibrinogen and/or Factor VIII and/or VWF is passed through the anion exchange chromatographic resin, the fibrinogen and/or Factor VIII and/or VWF bind(s) to the positively-charged functional groups attached to the resin, allowing impurities in the solution to pass through the resin in the flow-through (drop-through) fraction, where they can be discarded or recovered for other purposes. Once the flow-through fraction passes through the resin, the anion exchange chromatographic resin can be washed with a suitable wash buffer known to persons skilled in the art. The constituents of the wash buffer and the conditions of the wash step will typically be selected to retain the fibrinogen and/or Factor VIII and/or VWF bound to the resin during the wash step. The skilled person will also recognize that reference to wash buffer, elution buffer or similar in relation to chromatography can include solutions that have limited or no buffering capacity.

In an embodiment disclosed herein, prior to eluting the fibrinogen and/or Factor VIII and/or VWF from the anion exchange chromatographic resin, the resin is washed with a wash solution comprising epsilon-aminocaproic acid (ε-ACA). The addition of ε-ACA to the wash buffer can promote the elution of proteases (such as plasminogen) that may be bound to the anion exchange chromatographic resin during the first pass. An example of a suitable wash step is described in U.S. Pat. No. 6,960,463.

For eluting the fibrinogen and/or Factor VIII and/or VWF that remains bound to the anion exchange chromatographic resin, any suitable elution buffer known to persons skilled in the art can be used. For the removal of plasminogen and/or t-PA and/or other protease(s) from a solution comprising fibrinogen, the present inventors have found that an elution buffer comprising from about 150 mM to about 300 mM NaCl allows fibrinogen monomers to be eluted from the anion exchange resin while minimizing the elution of fibrinogen aggregates and/or other proteins (e.g., Factor VIII, VWF, fibronectin or proteases) that may be also bound to the resin. Thus, in an embodiment disclosed herein, the fibrinogen is eluted from the anion exchange resin with an elution buffer comprising from about 150 mM to about 300 mM NaCl. This equates to an elution buffer having a conductivity range of about 18 mS/cm (150 mM NaCl) to about 32 mS/cm (300 mM NaCl).

In another embodiment, the fibrinogen is eluted from the anion exchange resin with an elution buffer comprising from about 150 mM to about 270 mM NaCl. This equates to an elution buffer having a conductivity range of about 18 mS/cm (150 mM NaCl) to about 29 mS/cm (270 mM NaCl).

In another embodiment, the fibrinogen is eluted from the anion exchange resin with an elution buffer comprising from about 170 mM to about 230 mM NaCl. This equates to an elution buffer having a conductivity range of about 19 mS/cm (170 mM NaCl) to about 25 mS/cm (230 mM NaCl).

In another embodiment, the fibrinogen is eluted from the anion exchange resin with an elution buffer comprising from about 200 mM to about 220 mM NaCl. This equates to an elution buffer having a conductivity range of about 22 mS/cm (200 mM NaCl) to about 24 mS/cm (220 mM NaCl).

In another embodiment, the fibrinogen is eluted from the anion exchange resin with an elution buffer comprising from about 190 mM to about 210 mM NaCl.

In another embodiment, the fibrinogen is eluted from the anion exchange resin with an elution buffer comprising from about 150 mM to about 190 mM NaCl.

In another embodiment the elution buffer has a conductivity in the range of 18 to 32 mS/cm; or 20 to 25 mS/cm; or 21 to 23.5 mS/cm; or 22 to 23 mS/cm. In a preferred embodiment the conductivity of the elution buffer is about 22.5 mS/cm.

In an embodiment disclosed herein, the elution buffer comprises a free amino acid at a concentration that promotes the elution of fibrinogen monomer over aggregates thereof. In another embodiment, the elution buffer comprises a free amino acid at a concentration of about 0.5 to 10% (w/w). Any suitable free amino acid may be used in this capacity.

In an embodiment, the free amino acid is arginine. In another embodiment the elution buffer comprises arginine in the range of about 4 to about 10% (w/w).

In other embodiments the elution buffer comprises 200 mM NaCl, 0.5% (w/w) arginine; or 160 mM NaCl, 1% (w/w) arginine.

In an embodiment, anion exchange chromatography is performed in negative mode with respect to the fibrinogen and positive mode in respect to Factor VIII and/or VWF. That is, the conditions used are such that, when the solution or feedstock comprising fibrinogen and Factor VIII and/or VWF is passed through the anion exchange chromatographic resin, the Factor VIII and/or VWF bind(s) to the positively-charged functional groups attached to the resin, allowing fibrinogen in the solution to pass through the resin in the flow-through (drop-through) fraction. Once the fibrinogen containing flow-through fraction passes through the resin, the anion exchange chromatographic resin can be washed with a suitable wash buffer known to persons skilled in the art. The constituents of the wash buffer and the conditions of the wash step will typically be selected to retain the Factor VIII and/or VWF bound to the resin during the wash step.

In an embodiment, the solution or feedstock comprising fibrinogen and/or Factor VIII and/or VWF is passed through the anion exchange chromatographic resin in the presence of about 150 mM to about 270 mM NaCl. This equates to a conductivity range of about 18 mS/cm (150 mM NaCl) to about 29 mS/cm (270 mM NaCl). Under these conditions the fibrinogen particularly the monomeric form, passes through the anion exchange chromatographic resin whilst fibrinogen containing aggregates and other impurities such as IgG and fibronectin bind to the resin. In further embodiments the solution or feedstock comprising fibrinogen and/or Factor VIII and/or VWF is passed through the anion exchange chromatographic resin in the presence of about 170 mM to about 230 mM NaCl (about 19 mS/cm to about 25 mS/cm) or about 200 mM to about 220 mM NaCl (about 22 mS/cm to about 24 mS/cm). Under these types of conditions it is expected that Factor VIII and/or vWF will bind to the anion exchange chromatographic resin.

Factor VIII and/or VWF can be eluted from the anion exchange resin with an elution buffer comprising at least 300 mM of a salt such as NaCl. In a particular embodiment Factor VIII and/or VWF are eluted from the anion exchange resin with about 500 mM NaCl. Where fibrinogen and Factor VIII and/or VWF are bound to the anion exchange resin, the elation step can be conducted such that the fibrinogen is initially eluted (for example using conditions set out in the embodiments above) and then the Factor VIII and/or VWF can be eluted using a higher concentration of salt such as 500 mM NaCl.

Where an anion exchange chromatography step is employed, it can be performed either before and/or after passing the feedstock comprising fibrinogen and/or Factor VIII and/or VWF through the HCIC resin. In an embodiment disclosed herein, the method further comprises passing the solution comprising fibrinogen and/or Factor VIII and/or VWF that is recovered in step (ii) through an anion exchange chromatographic resin. In another embodiment, where first and second HCIC chromatographic steps are employed, as herein described, the method further comprising passing the solution comprising fibrinogen and/or Factor VIII and/or VWF that is recovered in step (ii) and/or step (iv) through an anion exchange chromatographic resin.

In an embodiment disclosed herein, the method further comprises passing the feedstock comprising fibrinogen and/or Factor VIII and/or VWF through an anion exchange chromatographic resin prior to step (i).

Persons skilled in the art will understand that the number of additional chromatographic steps used in accordance with the present invention will depend on the level of purity required in the final preparation. For example, the method of the present invention may comprise 2, 3, 4 or 5 chromatography steps, as disclosed herein. For example, where the method comprises 2 chromatography steps, the sequence of steps will be HCIC/IEX or HCIC/HCIC or IEX/HCIC; where the method comprises 3 chromatography steps, the sequence of steps will be HCIC/IEX/HCIC or HCIC/HCIC/IEX or HCIC/HCIC/HCIC or HCIC/IEX/IEX or IEX/HCIC/HCIC or IEX/HCIC/IEX or IEX/IEX/HCIC; where the method comprises 4 chromatography steps, the sequence of steps will be HCIC/IEX/HCIC/HCIC or HCIC/HCIC/IEX/HCIC or HCIC/HCIC/HCIC/IEX or HCIC/HCIC/HCIC/HCIC or HCIC/IEX/IEX/HCIC or HCIC/IEX/IEX/IEX or HCIC/HCIC/IEX/IEX or HCIC/IEX/HCIC/IEX or IEX/HCIC/IEX/HCIC or IEX/HCIC/HCIC/IEX or IEX/HCIC/HCIC/HCIC or IEX/HCIC/IEX/IEX or IEX/IEX/HCIC/HCIC or IEX/IEX/HCIC/IEX or IEX/IEX/IEX/HCIC; and so forth (where "IEX" denotes anion exchange chromatography). The required level of purity may be dictated by the intended use of the solution (e.g., for treatment of patient with a fibrinogen and/or Factor VIII and/or VWF deficiency) and/or where a longer storage period is required as an aqueous preparation.

Chromatography can be performed using any means known to persons skilled in the art. For example, the chromatography steps according to the present invention can use axial flow columns, such as those available from GE Healthcare, Pall Corporation and Bio-Rad, or radial flow columns, such as those available from Proxcys. The chromatography steps according to the present invention can also be conducted using expanded bed technologies.

In an embodiment, the concentration of the plasminogen and/or tissue plasminogen activator and/or other protease(s) in the recovered solution comprising fibrinogen and/or Factor VIII and/or VWF is reduced by at least 60%, by at least 70%, by at least 80%, or by at least 90% or by at least 95% compared to the feedstock.

Methods that maximize the removal of impurities such as plasminogen and/or tissue plasminogen activator and/or other protease(s) are particularly advantageous, because the stability and efficacy of the fibrinogen and/or Factor VIII and/or VWF in solution is decisively improved, particularly during long-term storage. Storage in liquid form is particularly advantageous for solutions comprising fibrinogen and/or Factor VIII and/or VWF because immediate use in a patient is possible. This is in contrast to the use of lyophilised preparations of purified fibrinogen and/or Factor VIII and/or VWF, which require reconstituting the lyophilized protein(s) in a suitable buffer and/or water for injection immediately prior to administration into a subject in need thereof.

An advantage of depleting proteases or their zymogens (such as plasminogen) from a solution comprising fibrinogen and/or Factor VIII and/or VWF is that it minimises the need to add anti-fibrinolytic agents to inhibit any residual protease and/or zymogen (e.g., plasmin or plasminogen). Examples of such agents include aprotinin, a bovine protein inhibitor of plasmin; ortranexamic acid, a synthetic plasmin inhibitor also associated with neurotoxic side-effects.

A further advantageous feature is that plasminogen, which has been separated from the solution comprising fibrinogen and/or Factor VIII and/or VWF by HCIC, may be further processed to yield a plasminogen-containing concentrate for, for example, clinical use. HCIC may therefore be used to prepare both plasminogen and solutions comprising fibrinogen and/or Factor VIII and/or VWF from a single starting solution.

A further advantageous feature is that the production costs of the HCIC resin is far more economical than the cost of lysine-SEPHAROSE™ or immobilised lysine resin which are used in affinity chromatography procedures.

A further advantageous feature is that the HCIC could be used, to replace aluminium hydroxide (e.g. ALHYDROGEL™) steps for the removal of proteases (e.g. Factor II). ALHYDROGEL™ is currently widely used in the commercial production of Factor VIII and VWF. The material is, however, relatively costly with 100 kg's typically used per batch. Moreover, ALHYDROGEL™ often requires manual handling and the material is discarded after a single use. In contrast, HCIC steps can be fully automated and the resin can be used in the manufacture of multiple batches.

Another advantageous feature is that the HCIC resin is compatible with 1M NaOH which can be used for inactivation and removal of pathogens including viruses and prions during column cleaning and resin sanitisation procedures.

Liquid preparations derived from the methods of the present invention also have advantages over the use of frozen preparations, which require expensive storage and transport means and must be thawed prior to immediate use. Even where the fibrinogen and/or Factor VIII and/or VWF is stored as a lyophilized or frozen preparation, it is advantageous for the reconstituted or thawed protein to be stable for longer. This is evident, for example, where material has been reconstituted as a precaution for a medical procedure, but its use was not required on the basis of medical considerations. This material is typically discarded, as the fibrinogen is only stable over a short-term period due to the presence of prothrombin and/or t-PA and/or other protease(s).

In particular embodiments the liquid preparations of the present invention containing fibrinogen and/or Factor VIII and/or VWF are stored as a liquid or a lyophilized or a frozen preparation.

In another aspect of the present invention, there is provided a method for purifying fibrinogen, the method comprising the steps of:
(i) passing a solution comprising fibrinogen through an ion exchange chromatographic resin under conditions selected such that fibrinogen monomer is bound to the resin;
(ii) eluting the fibrinogen monomer from the resin with an elution buffer; and
(iii) filtering the eluted fibrinogen monomer from step (ii) through a filter having a pore size in the range from about 15 nm to about 35 nm.

In an embodiment the solution comprising fibrinogen (step (i)) is recovered after passing a feedstock comprising fibrinogen through a hydrophobic charge-induction chromatographic resin under conditions selected such that the plasminogen and/or tissue plasminogen activator and/or other protease(s) is bound to the resin and the fibrinogen passes through the resin.

In an embodiment the ion exchange chromatographic resin is selected from an anion exchange chromatographic resin or a cation exchange chromatographic resin.

In an embodiment the anion exchange chromatographic resin is a strong anion exchange chromatographic resin or a weak anion exchange chromatographic resin. In an embodiment the anion exchange chromatographic resin comprises a quaternary amino group. Examples include quaternary alkylamine and quaternary alkylalkanol amine, or amine, diethylamine, diethylaminopropyl, amino, trimethylammoniumethyl, trimethylbenzyl ammonium, dimethylethanolbenzyl ammonium, and polyamine. In some embodiments the anion exchange chromatographic resin is a polymer support grafted with tertiary or quaternary amines or is a hydroxylated polymer support grafted with tertiary or quaternary amines. In some embodiments the anion exchange chromatographic resin comprises a methacrylate polymer support. In an embodiment the anion exchange chromatographic resin is a MACROPREP™ HQ. In another embodiment the anion exchange chromatographic resin is a GIGACAP™ Q-650M. In other embodiments the anion exchange chromatographic resin is packed into a column.

If desirable, an anion exchange chromatography membrane can be used instead of an anion exchange chromatography resin. Commercially available anion exchange chromatography membranes include, but are not limited to, SARTOBIND™ Q from Sartorius, MUSTANG™ Q from Pall Technologies and INTERCEPT™ Q membrane from Millipore.

In an embodiment the cation exchange chromatographic resin is a strong cation exchange chromatographic resin or a weak cation exchange chromatographic resin.

Commercially available cation exchange chromatography resins include, but are not limited to, for example, those having a sulfonate based group (e.g., MonoS, MiniS, SOURCE™ ISS and 30S, SP SEPHAROSE™ Fast Flow, SP SEPHAROSE™ High Performance from GE Healthcare, TOYOPEARL™ SP-650S and SP-650M from Tosoh, MACROPREP™ High S from BioRad, Ceramic HYPERD™ S, TRISACRYL™ M and LS™ SP and SPERODEX™ LS SP from Pall Technologies); a sulfoethyl based group (e.g., FRACTOGEL™ SE from EMD, POROS™ S-10 and S-20 from Applied Biosystems); a sulphopropyl based group (e.g., TSK™ Gel SP 5PW and SP-5PW-HR from Tosoh, POROS™ HS-20 and HS 50 from Applied Biosystems); a sulfoisobutyl based group (e.g., FRACTOGEL™ EMD S03" from EMD); a sulfoxyethyl based group (e.g., SE52, SE53 and EXPRESS-ION™ S from Whatman), a carboxymethyl based group (e.g., CM SEPHAROSE™ Fast Flow, from GE Healthcare, HYRDROCELL™ CM from Biochrom Labs Inc., MACRO-PREP™ CM from BioRad, Ceramic HYPERD™ CM, TRISACRYL™ M CM, TRISACRYL™ LS CM, from Pall Technologies, Matrex CELLUFINE™ C500 and C200 from Millipore, CM52™, CM32™, CM23™ and EXPRESS-ION™ C from Whatman, TOYOPEARL™ CM-650S, CM-650M and CM-650C from Tosoh); sulfonic and carboxylic acid based groups (e.g., BAKERBOND™ Carboxy-Sulfon from J. T. Baker); a carboxylic acid based group (e.g., WP™ CBX from J. T Baker, DOWEX MAC-3™ from Dow Liquid Separations, AMBDERLITE™ Weak Cation Exchangers, DOWEX™ Weak Cation Exchanger, and DIAION™ Weak Cation Exchangers from SigmaAldrich and FRACTOGEL™ EMD COO— from EMD); a sulfonic acid based group (e.g., HYRDROCELL™ SP from Biochrom Labs Inc., DOWEX™ Fine Mesh Strong Acid Cation Matrix from Dow Liquid Separations, UNOSPHERE™ S, WP Sulfonic from J. T. Baker, SARTOBIND™ S membrane from Sartorius, AMBDERLITE™ Strong Cation Exchangers, DOWEX™ Strong Cation and DIAION™ Strong Cation Exchanger from Sigma-Aldrich); and a orthophosphate based group (e.g., PI 1 from Whatman). If desirable, a cation exchange chromatography membrane can be used instead of a cation exchange matrix, e.g., SARTOBIND™ S (Sartorius; Edgewood, N.Y.).

In an embodiment the solution comprising fibrinogen has a pH in the range of about pH 7 to pH 10. In an embodiment, the pH of the solution comprising fibrinogen is about pH 8. In some embodiments, the anion exchange chromatographic resin will be pre-equilibrated and washed after loading of the fibrinogen with buffer/s having a similar pH to the solution comprising the fibrinogen.

In an embodiment the elution buffer has a conductivity in the range from about 18 to about 30 mS/cm. For example, the conductivity of the elution buffer may be in the range of about 18 to about 25 mS/cm; or about 19 to about 24 mS/cm; or about 20 to about 24 mS/cm; or about 21 to about 23 mS/cm. In an embodiment, the conductivity of the elution buffer is about 22 mS/cm. In other embodiments the elution buffer comprises NaCl. In an embodiment the elution buffer comprises NaCl at a concentration in the range of about 180 mM to about 230 mM, or about 190 mM to about 210 mM. In an embodiment the NaCl concentration in the elution buffer is about 200 mM.

In an embodiment the elution buffer comprising the fibrinogen contains a protein concentration of about 0.5 to about 10 mg/mL. In some embodiments the protein concentration of the elution buffer comprising the fibrinogen is in the range from about 4 to about 8 mg/mL. In particular embodiments the elution buffer comprising the fibrinogen is about 6 mg/mL.

In an embodiment the eluted fibrinogen monomer is formulated with one or more amino acids prior to filtering (step (iii)). In an embodiment the amino acid is arginine or glycine or a combination thereof. In some embodiments the concentration of the amino acid in the elution buffer comprising fibrinogen is in the range of about 0.5 to about 10% (w/w). In an embodiment the concentration of the amino acid in the elution buffer comprising fibrinogen is about 1% to about 6% (w/w), or about 2% to about 6% (w/w) or about 2% to about 5% (w/w). In an embodiment the elution buffer comprising the fibrinogen is formulated with about 2%, or about 3%, or about 4% or about 5% (w/w) arginine.

In an embodiment the eluted fibrinogen monomer has a pH from about pH 7 to about pH 9.

In an embodiment the filter of step (ii) has a pore size in the range from about 15 nm to about 35 nm; or from about 15 nm to about 30 nm; or from about 15 nm to about 25 nm; or from about 15 nm to about 20 nm.

The virus filtration can be performed using either tangential flow filtration (TFF) or 'dead-end' filtration (also known as normal flow filtration). Virus filters were originally designed for use in TFF with the feed flowing adjacent to the upper skin layer of the asymmetric membrane. TFF provides high flux by sweeping the membrane surface to reduce concentration polarization and fouling. However, the simplicity and lower capital cost of dead end filtration has led to the widespread use of virus filters specifically designed for dead end filtration. In contrast to TFF, these dead-end filters are typically operated with the more open side of the membrane facing the feed stream, allowing protein aggregates and other large foulants to be captured within the macroporous substructure thereby protecting the virus-retentive skin layer. Advantages of using single-use dead end filters include that they simplify both system design and validation, reducing labor and capital costs.

Dead-end filtering typically involves using a single pump to force fluid through the membrane from the surface. Tangential filtration generally requires a first pump to maintain constant flow rate at the surface of the filter membrane and a second pump draws the protein through the membrane by creating a negative pressure at the back of the membrane.

In an embodiment the filtration is performed by dead-end filtration.

In an embodiment the dead-end filtration process is conducted using either constant pressure filtration or constant velocity filtration. In an embodiment, the dead-end filtration process is conducted using constant pressure filtration.

Filtration is typically performed with filtration pressure that is the same as or below the level at which the membrane can withstand, depending on the material of a virus-removing membrane to be used herein, for example with pressures of about 0.2 to about 3.4 bar. In an embodiment the filtration pressure is maintained between about 0.2 bar to about 3.4 bar. In another embodiment the filtration pressure is maintained at about 1 to about 3 bar; or at about 1 to about 2 bar; or at about 1.2 to about 2 bar. In another embodiment the filtration pressure is maintained at about 1.5 bar to about 1.9 bar.

Temperature may have an effect on the viscosity of a protein solution and on the flux upon filtration with a virus-removing membrane. It would be understood by those skilled in the art that the solution to be used in the filtration step would typically have a temperature within the range from about 0° C. up to the temperature at which the protein of interest is denatured. The temperature of the solution suitably lies within the range of from about 10° C. up to about 50° C. In an embodiment the temperature of the solution lies within the range of from about 18° C. up to about 35° C. In another embodiment the solution is filtered at room temperature from about 18° C. to about 26° C.

In an embodiment the virus filter capacity is at least 0.20 kg or at least 0.50 kg or at least 0.75 kg or at least 1.00 kg or at least 1.25 kg or at least 1.50 kg or at least 2 kg of fibrinogen per $m^2$ of filter surface area.

Optionally, a pre-filtration or clarifying filtration step can be performed before the virus filtration in order to remove macro-size particles. In an embodiment, a pre-filtration is performed with a pre-filter comprising a membrane with a larger pore diameter than that of the virus-removing membrane. In an embodiment the pre-filter is a membrane filter has a pore size of about 0.1 μm. In another embodiment the pre-filter is selected from Pall Nylon membrane filter (SKL 7002 NTP 0.1 μm or FTKNI), or other pre-filters commercially available having similar properties for the removal of protein aggregates and/or particulates. Pre-filtration can be conducted either in line with the virus filter or out of line with respect to the virus filter. In an embodiment the pre-filtration is conducted in line with respect to the virus filter.

Suitable filters for the virus filtration method according to this aspect of the invention would be known to persons skilled in the art. An example includes Planova BIOEX™, inter alia. Such filters are sometimes referred to as 'small virus' removal filters.

In an embodiment the filter membrane is a flat sheet or a hollow fibre membrane. Examples of flat sheet membranes include hydrophilised PVDF filter membranes such as the PEGASUS™ Grade SV4 small-virus removal filters (Pall Corporation). In an embodiment, the filter is the PEGASUS™ Grade SV4.

In other embodiments the filter is a hollow fibre membrane. A hollow fibre membrane may contain a bundle of straw-shaped hollow fibres with the wall of each hollow fibre containing a 3 dimensional web structure of pores comprised of voids interconnected by fine capillaries. Examples of hollow fibre filters include the PLANOVA™ BIOEX™ filters (Asahi Kasei Corporation) which incorporates hydrophilic modified polyvinylidene fluoride (PVDF) in hollow fiber membrane format. In an embodiment, the filter is the PLANOVA™ BIOEX™.

In an embodiment two or more small virus filters are used in series. In an embodiment the filtration is conducted using two filters in series having a pore size in the range from about 15 to about 20 nm. Such filtration steps have the potential to enable fibrinogen to be manufactured with at least LRV 6.9 log LRV for parvoviruses-like MVM.

In another aspect of the present invention, the solution comprising fibrinogen is passed through an ion exchange chromatographic resin under conditions selected such that fibrinogen present in the solution passes through the resin. That is, the ion exchange chromatography is performed in negative mode with respect to fibrinogen under conditions such that, when the solution is passed through the resin, impurities such as fibrinogen aggregates, plasminogen and fibronectin present in the solution bind(s) to the charged functional groups attached to the resin, allowing fibrinogen present in the solution, particularly fibrinogen monomer, to pass through the resin in the flow-through (drop-through) fraction. Once the fibrinogen containing flow-through fraction passes through the resin, the ion exchange chromatographic resin can be washed with a suitable wash buffer known to persons skilled in the art. The constituents of the wash buffer and the conditions of the wash step will typically be selected to retain the impurities bound to the resin during the wash step.

In an embodiment, the ion exchange chromatographic resin is selected from an anion exchange chromatographic resin or a cation exchange chromatographic resin.

In an embodiment, the solution comprising fibrinogen is passed through an anion exchange chromatographic resin in the presence of about 150 mM to about 270 mM NaCl. This equates to a conductivity range of about 18 mS/cm (150 mM NaCl) to about 29 mS/cm (270 mM NaCl). Under these conditions the fibrinogen, particularly the monomeric form, passes through the anion exchange chromatographic resin whilst fibrinogen containing aggregates and other impurities such as plasminogen and fibronectin bind to the resin. In further embodiments, the solution comprising fibrinogen is passed through the anion exchange chromatographic resin in the presence of about 170 mM to about 230 mM NaCl (about 19 mS/cm to about 25 mS/cm) or about 200 mM to about 220 mM NaCl (about 22 mS/cm to about 24 mS/cm). Under these types of conditions it is expected that the impurities will bind to the anion exchange chromatographic resin, allowing fibrinogen to pass through the resin in the flow-through fraction.

The solution comprising fibrinogen and/or Factor VIII and/or VWF recovered by the methods of the present invention are advantageous because they provide a preparation of fibrinogen and/or Factor VIII and/or VWF that has greater stability than existing lyophilised preparations, even at room temperature. This can be particularly advantageous on lengthy transport routes where low temperatures may, where appropriate, not be ensured throughout transport and/or storage. Stable storage of fibrinogen and/or Factor VIII and/or VWF in solution also facilitates, in many respects, the production, usage, transport and administration to a patient in need thereof. Owing to the increased stability of the fibrinogen and/or Factor VIII and/or VWF prepared in accordance with the present invention, it is possible in many pharmaceutical preparations to dispense with the addition of stability agents, such as fibrinolysis or fibrinogenolysis inhibitors that may, in some circumstances, lead to unwanted side effects or which should be avoided to reduce potential risks.

The term "stable", as used herein, means that there is little or no substantial loss of activity of the fibrinogen and/or Factor VIII and/or VWF after a period of time in storage as compared to the level of activity of the fibrinogen and/or Factor VIII and/or VWF before storage (e.g., as compared to the level of activity determined immediately after recovery of the solution comprising fibrinogen and/or Factor VIII and/or VWF in accordance with the present invention). In an embodiment disclosed herein, the solution comprising fibrinogen and/or Factor VIII and/or VWF retains at least 70% activity, preferably at least 80% activity, more preferably at least 90% activity, even more preferably at least 95% activity and most preferably 100% activity after a period of time in storage at a temperature of about 0° C. to about 30° C. The skilled person will understand that fibrinogen activity can be determined for the fibrinogen preparation immediately prior to beginning the storage period and this initial value can be used to designate 100% activity from which the fibrinogen activity determined at different time points during the storage period can be compared and expressed as a percentage of this initial value.

In an embodiment disclosed herein, the fibrinogen recovered by the methods of the present invention retains from about 90% to 100% activity after at least 4 weeks in storage of the solution at a temperature of about 2° C. to about 8° C., preferably retains about 90% activity after 4 weeks in storage of the solution at a temperature of about 2° C. to about 8° C. In another embodiment disclosed herein, the fibrinogen retains from about 60% to about 80% activity after at least 4 weeks in storage of the solution at a temperature of about 30° C., preferably retains from about 60% to about 70% activity after 5 weeks in storage of the solution at a temperature of about 30° C. The level of activity of the fibrinogen and/or Factor VIII and/or VWF can be determined by any means known to persons skilled in the art. Examples of suitable methods for determining the activity of fibrinogen, for example, are summarised by Mackie et al. (*British J. Haematol.* 121:396-404, 2003). Particular methods include Clauss (Clauss, 1957, Acta-Haematol. 17, 237-246) and/or clottable protein (Jacobsson K., Scand J Clin Lab Invest 1955; 7 (supp 14):1-54 or Fibrin sealant Ph. Eur. Monograph 903, 2012). Results can be reported as % clottable protein; % of initial clottable protein, and/or % of initial fibrinogen activity as determined using the Clauss method or similar.

The skilled person will understand that the concentration of the plasminogen and/or tissue plasminogen activator and/or other protease(s) in the recovered solution comprising fibrinogen and/or Factor VIII and/or VWF is likely to dictate the length of storage and/or storage conditions (e.g., temperature). For example, it will be understood that a preparation in which the concentration of the plasminogen and/or tissue plasminogen activator and/or other protease(s) in the recovered solution is reduced by 80% compared to the feedstock may be stored for a longer period of time and/or at higher temperatures without significantly destabilising the activity of the fibrinogen and/or Factor VIII and/or VWF as compared to a preparation in which the concentration of the plasminogen and/or tissue plasminogen activator and/or other protease(s) in the recovered solution comprising fibrinogen and/or Factor VIII and/or VWF is reduced by only 50% compared to the feedstock.

Whilst the methods of the present invention can be performed at laboratory scale, they can be scalable up to industrial size without significant changes to conditions. Thus, in an embodiment disclosed herein, the methods of the present invention are performed on an industrial or commercial scale. Preferably, the methods of the invention are suitable for the commercial scale manufacture of fibrinogen and/or Factor VIII and/or VWF. For example, when using plasma fractions as a starting material in the method of the invention, then commercial scale manufacture would involve the use of a plasma fraction derived from at least about 500 kg of plasma. More preferably, the starting plasma fraction will be derived from at least about 5,000 kg, 7,500 kg, 10,000 kg and/or 15,000 kg of plasma per batch. In particular embodiments, the solutions and pharmaceutical formulations comprising fibrinogen and/or Factor VII and/or VWF of the present invention are manufactured at commercial scale from a plasma fraction or a recombinant feedstock.

Where a solution comprising fibrinogen and/or Factor VIII and/or VWF is to be used for clinical or veterinary applications (e.g., for administration to a subject with fibrinogen and/or Factor VIII and/or VWF deficiency or for use as a fibrin glue), persons skilled in the art will understand that it may be desirable to reduce the level of active virus content (virus titre) and other potential infectious agents (for example prions) in the solution. This may be particularly desirable where the feedstock comprising fibrinogen and/or Factor VIII and/or VWF (i.e., the starting material) is derived from blood plasma. Methods of reducing the virus titre in a solution will be known to persons skilled in the art. Examples include pasteurization (for example, incubating the solution at 60° C. for 10 hours in the presence of high concentrations of stabilisers such as glycine (e.g. 2.75M) and sucrose (e.g. 50%) and/or other selected excipients or salts), dry heat treatment, virus filtration (passing the solution through a nano-filter; e.g., 20 nm cutoff) and/or subjecting the solution to treatment with a suitable organic solvent and detergent for a period of time and under conditions to inactivate virus in the solution. Solvent detergent has been used for over 20 years to inactivate enveloped viruses particularly in plasma-derived products including fibrinogen and factor VIII and/or VWF. Thus it may be carried out using various reagents and methods known in the art (see, for example, U.S. Pat. No. 4,540,573 and U.S. Pat. No. 4,764,369 which are hereby incorporated by reference). Suitable solvents include tri-n-butyl phosphate (TnBP) and ether, preferably TnBP (typically at about 0.3%). Suitable detergents include polysorbate (Tween) 80, polysorbate (Tween) 20 and Triton X-100 (typically at about 0.3%). The selection of treatment conditions including solvent and detergent concentrations depend in part on the characteristics of the feedstock with less pure feedstocks generally requiring higher concentrations of reagents and more extreme reaction conditions. A preferred detergent is polysorbate 80 and a particularly preferred combination is polysorbate 80 and TnBP. The feedstock may be stirred with solvent and detergent reagents at a temperature and for a time sufficient to inactivate any enveloped viruses that may be present. For example, the solvent detergent treatment may be carried out for about 4 hours at 25° C. The solvent detergent chemicals are subsequently removed by for example adsorption on chromatographic media such as C-18 hydrophobic resins or eluting them in the drop-through fraction of ion exchange resins under conditions which adsorb the protein of interest.

The virus inactivation step can be performed at any suitable stage of the methods disclosed herein. In an embodiment, the feedstock comprising fibrinogen and/or Factor VIII and/or VWF is subject to a viral inactivation step prior to step (i). In another embodiment, the solution comprising fibrinogen and/or Factor VIII and/or VWF that is recovered from the hydrophobic charge-induction chromatographic resin (i.e., from steps (ii) and/or (iv)) is subject to a viral inactivation step. In an embodiment disclosed herein, the viral inactivation step comprises pasteurization or treatment with an organic solvent and detergent. In another embodiment disclosed herein, the virus inactivation step comprises virus filtration. Where virus filtration is used, the inventors have found that the addition of a free amino acid (e.g., arginine) prior to the filtration step can significantly improve the flux rate and recovery of fibrinogen and/or Factor VIII and/or VWF through the filter. An example of such method is described in U.S. Pat. No. 7,919,592.

In an embodiment disclosed herein, the feedstock or solution comprising fibrinogen and/or Factor VIII and/or VWF is subject to a viral inactivation step before it is passed through the anion exchange chromatographic resin. The advantage of employing a virus inactivation step such as solvent detergent treatment prior to passing the treated solution or feedstock through an anion exchange chromatographic resin is that the anion exchange resin allows for the removal of the organic solvent and detergent from the treated solution by utilizing conditions that promote binding of the fibrinogen and/or Factor VIII and/or VWF to the resin and removal of the organic solvent and detergent with the flow-through (drop-through) fraction.

Pasteurization can generate protein aggregates and polymers, particularly in a solution comprising fibrinogen (also referred to herein as a "fibrinogen solution"). Therefore, it may be desirable in some instances to reduce the level of aggregates/polymers in a pasteurized solution. This can be achieved by any means knows to persons skilled in the art, although conveniently can be achieved by further chromatographic purification. In an embodiment disclosed herein, the pasteurized solution or feedstock is passed through an anion exchange chromatographic resin in positive mode with respect to the fibrinogen and/or Factor VIII and/or VWF such that any aggregates or polymers are removed with the flow-through (drop-through) fraction.

The term "feedstock" is used herein to denote any solution comprising fibrinogen and/or Factor VIII and/or VWF. The feedstock may also comprise other proteins (e.g., therapeutic proteins) known to persons skilled in the art. Examples include proteins involved in the blood coagulation cascade. In an embodiment disclosed herein, the feedstock comprises fibrinogen.

Suitable feedstock comprising fibrinogen and/or Factor VIII and/or VWF will be known to persons skilled in the art. Examples include plasma or plasma fractions such as solubilised plasma cryoprecipitate or solubilised Fraction I paste derived from human or animal plasma or a plasma fraction, cell culture fractions from recombinant technology, fractions derived from milk from transgenic animals, etc. Sources of recombinant fibrinogen and/or Factor VIII and/or VWF proteins are also suitable for use as a feedstock in accordance with the present invention. Where the feedstock is plasma or a plasma fraction, it can be either pooled plasma donations or it can be from an individual donor. In an embodiment disclosed herein, the feedstock comprising fibrinogen and/or Factor VIII and/or VWF is a solubilised plasma cryoprecipitate. This component, either derived from whole blood or collected via apheresis, is prepared by controlled thawing fresh frozen plasma between 1-6° C. and recovering the precipitate. The cold-insoluble precipitate is refrozen. One unit of cryoprecipitate apheresis is approximately equivalent to 2 units of cryoprecipitate derived from whole blood. It contains most of the fibrinogen, Factor VIII and VWF along with other proteins such as factor XIII and fibronectin from fresh frozen plasma. An alternate source of fibrinogen is Fraction I precipitate which can be prepared from frozen plasma by thawing and removing the cryoprecipitate by either centrifugation or filtration. The resultant cryosupernatant is then mixed with ethanol to precipitate Fraction I. For example, a Fraction I precipitate can be obtained by adding about 8% (v/v) ethanol at pH 7.2 and controlling the temperature to about −3° C. (Cohn, et al. 1946, J. Am. Chem. Soc. 62: 459-475). In an embodiment, the feedstock comprising fibrinogen and/or Factor VIII and/or VWF is cryoprecipitate.

Reference in the specification to "protease(s)" can be to any protease and/or its zymogen present in the feedstock or solution comprising fibrinogen and/or Factor VIII and/or VWF that, when exposed to a HCIC resin, is capable of binding to HCIC resin under conditions where the fibrinogen and/or Factor VIII and/or VWF passes through the resin. Proteases may be any type, including serine proteases (e.g., plasmin, thrombin, trypsin), threonine proteases, cysteine proteases (e.g., cathepsin B and cathepsin H), aspartate proteases (e.g., pepsin), metallo-proteases (e.g., collagenases and gelatinases) and glutamic proteases. Where the feedstock comprising fibrinogen and/or Factor VIII and/or VWF is derived from human or animal plasma, the proteases/zymogens may include plasminogen, tissue plasminogen activator (tPA), thrombin, elastase, Factor VIIa, Factor IXa, Factor Xa, Factor XIa, Factor XIIa, Factor XIIIa, plasma kallikreins and the like. In regard to solutions comprising fibrinogen and/or Factor VIII and/or VWF, a particular preferred protease/zymogen to be removed is plasminogen. Other preferred proteases/zymogens to be removed from a solution comprising fibrinogen and/or Factor VIII and/or VWF are t-PA, pro- and/or active thrombin (Factor II/IIa). When the feedstock comprising fibrinogen and/or Factor VIII and/or VWF is derived from cell culture supernatant, the protease/zymogen can include any host cell protease, such as serine proteases (e.g., caseinases), metalloproteases (e.g., gelatinases, matrix metalloproteases (MMP) including MMP3, MMP10 or MMP2), aspartic proteases (cathepsin D), acid proteases amongst others.

In some instances, it may be desirable to remove or reduce the level of impurities from the feedstock before passing the feedstock through an HCIC resin in step (i). Removing or reducing the level of impurities from the feedstock can reduce the load on the HCIC resin during chromatographic purification and thus improve the efficiency of separation of plasminogen and/or tissue plasminogen activator and/or other protease(s) from the feedstock. Impurities may be removed or reduced, for example, by precipitating fibrinogen and/or Factor VIII and/or VWF from the feedstock and recovering the precipitated protein(s). Suitable methods of precipitating fibrinogen and/or Factor VIII and/or VWF from a feedstock comprising fibrinogen and/or Factor VIII and/or VWF will be known to persons skilled in the art. An example includes adding aluminium hydroxide suspension to the feedstock, which is particularly useful for removing vitamin K-dependent proteins (for example, the clotting factors II, VII, IX, and X) and other proteins that have binding affinity for aluminium hydroxide, such as prothrombin (factor II) and t-PA, from plasma or plasma cryoprecipitate.

Thus, in an embodiment disclosed herein, prior to step (i), vitamin K-dependent proteins are removed or reduced from the feedstock. In a further embodiment, vitamin K-dependent proteins are removed or reduced by addition of aluminium hydroxide to the feedstock. Aluminium hydroxide may be in the form of ANHYDROGEL®, added to the feedstock to a final concentration of about 10% to about 80% w/w. In some embodiments, the aluminium hydroxide is added to the feedstock to a final concentration in the range from about 10% to about 50% (w/w). In other embodiments, the aluminium hydroxide is added to the feedstock to a final concentration in the range from about 10% to about 30% (w/w). In preferred embodiments, the concentration is from about 15% to about 30% (w/w). Most preferably, the aluminium hydroxide is added to the feedstock at about 15% to about 25% (w/w) for optimum fibrinogen recovery and removal of impurities such as prothrombin. In another embodiment, vitamin K-dependent proteins are removed from the feedstock by batch adsorption using aluminium hydroxide.

In another aspect of the present invention, there is provided a solution comprising fibrinogen and/or Factor VIII and/or VWF that is recovered by the method of the present invention, as herein described. In an embodiment, the level of plasminogen and/or tissue plasminogen activator and/or other protease(s) in the solution will be less than 20% of total protein, preferably less than 10% of total protein, and more preferably less than 5% of total protein, or less than 1% of total protein, or less than 0.1% of total protein, or less than 0.01% of total protein or less than 0.001% of total protein, or less than 0.0001% of total protein. The skilled person will understand that the level of plasminogen and/or tissue plasminogen activator and/or other protease(s) that is present in the solution comprising fibrinogen and/or Factor VIII and/or VWF may depend on the intended use of the solution or length of storage. For example, where the solution is to be stored for at least 4 weeks at a temperature of about 0° C. to about 8° C., it may be acceptable that the solution comprises more than about 10% plasminogen and/or tissue plasminogen activator and/or other protease(s) (of total protein). Where the solution is to be stored for at least 4 weeks at a temperature of about 30° C., it may be desirable that the solution comprises less than about 10% plasminogen and/or tissue plasminogen activator and/or other protease(s) (of total protein).

In an embodiment disclosed herein, there is provided a solution comprising fibrinogen recovered by the method of the present invention. In another embodiment, the solution comprises at least 80% total protein of fibrinogen.

In another aspect of the present invention, there is provided a solution comprising:
(a) at least 75% total protein of fibrinogen;
(b) less than 50 pg/mg total protein of tissue plasminogen activator; and/or
(c) less than 1 µg/mg total protein of plasminogen.

In an embodiment, the solution further comprises less than $1.5 \times 10^{-5}$ U/mg total protein of Factor II.

In another aspect of the present invention, there is provided a solution comprising:
(a) at least 90% total protein of fibrinogen;
(b) less than 50 pg/mg total protein of tissue plasminogen activator, and/or
(c) less than 150 ng/mg total protein of plasminogen.

In an embodiment, the solution further comprises:
(a) less than $3.5 \times 10^{-6}$ U/mg total protein of Factor II; and/or
(b) less than 150 pg/mg total protein of fibronectin.

In another aspect of the present invention, there is provided a solution comprising:

(a) at least 90% total protein of fibrinogen;
(b) less than 50 pg/mg total protein of tissue plasminogen activator; and/or
(c) less than 10 ng/mg total protein of plasminogen.

In another aspect of the present invention, there is provided a solution comprising:
(a) at least 90% total protein of fibrinogen;
(b) less than 20 pg/mg total protein of tissue plasminogen activator; and/or
(c) less than 10 ng/mg total protein of plasminogen.

In an embodiment, the solution further comprises:
(a) less than $2.7 \times 10^{-6}$ U/mg total protein of Factor II; and/or
(b) less than 15 µg/mg total protein of fibronectin.

The concentration of the fibrinogen and/or Factor VIII and/or VWF in the solution recovered by the methods disclosed herein and the concentration of impurities (e.g., plasminogen and/or tissue plasminogen activator and/or other protease(s)) can be measured by any means known to persons skilled in the art. Examples of suitable assays for measuring fibrinogen are described by Mackie et al. (*Br J Haematol.* 2003 May; 121(3):396-404). Size exclusion HPLC may also be used to measure the concentration of fibrinogen and/or Factor VIII or an impurity in the solution comprising fibrinogen and/or Factor VIII (e.g., Cardinali et al. 2010, Arch. Biochem. Biphys. 493(2):157-168; and Kosloski et al. 2009, AAPS J. 11(3); 424-431). HPLC also allows the skilled person to discriminate between monomers and aggregates of fibrinogen. Moreover, the concentration of fibrinogen and/or Factor VIII and/or VWF may differ depending on the sensitivity of the assay that is used. For instance, the concentration of fibrinogen in a solution as measured using the Clauss assay may be slightly lower than the concentration as measured in the same solution by HPLC.

In an embodiment disclosed herein, the concentration of monomeric fibrinogen in the solution is at least 75%, at least 80%, at least 85%, at least 90% or at least 95% of total protein as measured by size exclusion HPLC.

In another aspect of the present invention, there is provided a pharmaceutical formulation comprising a solution comprising fibrinogen and/or Factor VIII and/or VWF recovered by the methods disclosed herein, and a pharmaceutically acceptable carrier. Suitable pharmaceutically acceptable carriers, including pharmaceutically acceptable diluents and/or excipients, will be known to those skilled in the art. Examples include solvents, dispersion media, antifungal and antibacterial agents, surfactants, isotonic and absorption agents and the like.

The pharmaceutical formulation may also be formulated by the addition of a combination of suitable stabilisers, for example, an amino acid, a carbohydrate, a salt, and a detergent. In particular embodiments, the stabiliser comprises a mixture of a sugar alcohol and an amino acid. The stabilizer may comprise a mixture of a sugar (e.g. sucrose or trehalose), a sugar alcohol (e.g. mannitol or sorbitol), and an amino acid (e.g. proline, glycine and arginine). In a preferred embodiment, the formulation comprises an amino acid such as arginine. In other embodiments, the formulation comprises divalent metal ions in a concentration up to 100 mM and a complexing agent as described in U.S. Pat. No. 7,045,601. Particular embodiments include formulations 1 to 7 as described in Example 1 of U.S. Pat. No. 7,045,601. In particular embodiments, the formulation is formulated without the addition of any anti-fibrinolytic agents or stabilising proteins such as albumin. In embodiments where the formulation comprises fibrinogen, the pH is preferably about 6.5 to 7.5 and the osmolality is at least 240 mosmol/kg.

The pharmaceutical formulation may also be sterilised by filtration prior to dispensing and long term storage. Preferably, the formulation will retain substantially its original stability characteristics for at least 2, 4, 6, 8, 10, 12, 18, 24, 36 or more months. For example, formulations stored at 2-8° C. or 25° C. can typically retain substantially the same molecular size distribution as measured by HPLC-SEC when stored for 6 months or longer. Particular embodiments of the pharmaceutical formulation can be stable and suitable for commercial pharmaceutical use for at least 6 months, 12 months, 18 months, 24 months, 36 months or even longer when stored at 2-8° C. and/or room temperature.

The solutions and pharmaceutical formulations of the present invention, as herein described, may be formulated into any of many possible dosage forms, such as injectable formulations. The formulations and their subsequent administration (dosing) are within the skill of those in the art. Dosing is dependent on the responsiveness of the subject to treatment, but will invariably last for as long as the desirable effect is required (e.g., a return to normal plasma levels of fibrinogen). Persons of ordinary skill can easily determine optimum dosages, dosing methodologies and repetition rates.

In an embodiment disclosed herein, the pharmaceutical formulation of the present invention has a volume of at least 5 mL and comprises at least 5 mg/mL fibrinogen. In another embodiment, the pharmaceutical formulation has a volume of at least 5 mL and comprises at least 20 mg/mL fibrinogen. In particular embodiments, the pharmaceutical formulation has a volume of at least 5 mL and comprises fibrinogen at a concentration of about 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 90 mg/mL or 100 mg/mL. In another aspect, there is provided a vessel containing at least 5 mL of a stable pharmaceutically acceptable fibrinogen solution, wherein the concentration of fibrinogen is at least 20 mg/mL.

In another aspect of the present invention, there is provided a method of treating or preventing a condition associated with fibrinogen and/or Factor VIII and/or VWF deficiency, the method comprising administering to a subject in need thereof a solution comprising fibrinogen and/or Factor VIII and/or VWF recovered by the method of the present invention, as herein disclosed, or the pharmaceutical formulation of the present invention, as herein disclosed.

In another aspect of the present invention, there is provided use of a solution comprising fibrinogen and/or Factor VIII and/or VWF recovered by the method of the present invention, as herein disclosed, in the manufacture of a medicament for treating or preventing a condition associated with fibrinogen and/or Factor VII and/or VWF deficiency. Persons skilled in the art will be familiar with the types of conditions associated with fibrinogen and/or Factor VIII and/or VWF deficiency. In an embodiment, the fibrinogen condition is selected from the group consisting of afibrinogenemia, hypofibrinogenemia and dysfibrinogenemia. In an embodiment the Factor VIII and/or VWF condition is selected from the group consisting of hemophilia A, bleeding disorders (e.g., defective platelet function, thrombocytopenia or von Willebrand's disease), vascular injury, bleeding from trauma or surgery, bleeding due to anticoagulant therapy, bleeding due to liver disease.

Other conditions that may be treatable with a solution comprising fibrinogen and/or Factor VIII and/or VWF recovered by the methods of the present invention, as herein disclosed, include major wounds and severe hemorrhaging and burns. In cases of hypofibrinogenamia and afibrinogenemia, a solution comprising fibrinogen prepared in accordance with the present invention can be injected intravenously into the patient in need thereof in order to compensate the state of fibrinogen deficiency and dosages can be determined by the skilled person based on the degree of deficiency.

A solution comprising fibrinogen recovered by the methods of the present invention also has advantages in the use of fibrin glues (also known as fibrin sealants) due to the lack of destabilizing levels of plasminogen and/or tissue plasminogen activator and/or other protease(s). tPA converts plasminogen to its active form plasmin which in turn digests the fibrin clot and therefore reduces clot formation upon topical application (e.g. for haemostasis).

Fibrin glues typically comprise two components: (i) fibrinogen (frequently together with factor XIII and a fibrinolysis inhibitor such as aprotinin), and (ii) thrombin (frequently together with calcium ions). The two components are reconstituted in order to prepare the glue ready for use. Fibrin glue is used in clinical and veterinary applications to simulate the last step of coagulation through the formation of cross-linked fibrin fibres using a combination of fibrinogen with thrombin in the presence of calcium and Factor XIII. Fibrin glue has diverse applications in clinical and veterinary medicine, including haemostasis, wound closure, adhesion prophylaxis and wound healing. Fibrin glue can also be used to close skin wounds (including skin transplant), for sealing sutures and for bonding connective tissues, such as bone, cartilage and tendons. Thus, in another aspect disclosed herein, there is provided a fibrin glue comprising the solution comprising fibrinogen recovered by the methods of the present invention, as herein disclosed.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1—Purification of Fibrinogen Through HEA, PPA and MEP Hydrophobic Charge Induction Chromatographic (HCIC) Resin Human pooled plasma cryoprecipitate was used as the starting material (i.e., fibrinogen-containing feedstock). Briefly, the pooled plasma cryoprecipitate was solubilised in an extraction buffer containing 20 mM Tri-sodium citrate, 200 mM epsilon-amino caproic acid (ε-ACA), 60 IU/mL heparin and 500 mM NaCl (pH 7.2±2) at 31±2° C. for 30 minutes (1 g cryoprecipitate per 4 g of buffer). Aluminium hydroxide 2% (w/w) was then added to the solubilised cryoprecipitate at a concentration of 25% (w/w). After which the aluminium hydroxide gel was removed by either centrifugation or depth filtration and the fibrinogen-containing supernatant was recovered for further chromatographic purification through a HCIC chromatographic resin.

The fibrinogen-containing supernatant was applied to chromatography columns that were packed with 1.8 mL of either HEA, PPA or MEP HYPERCEL™ resin. The chromatography columns were pre-equilibrated in 25 mM Tris at a different pH, ranging from 6.5 to 8.5. The fibrinogen-containing supernatant was loaded onto the chromatography column at a ratio of approximately 11 mL/mL resin. HCIC purification was performed in negative mode with respect to fibrinogen, in which fibrinogen was allowed to drop-through in the unbound flow-through fraction, whilst the majority of t-PA, plasminogen and Factor II remained bound to the resin.

Figure 2:
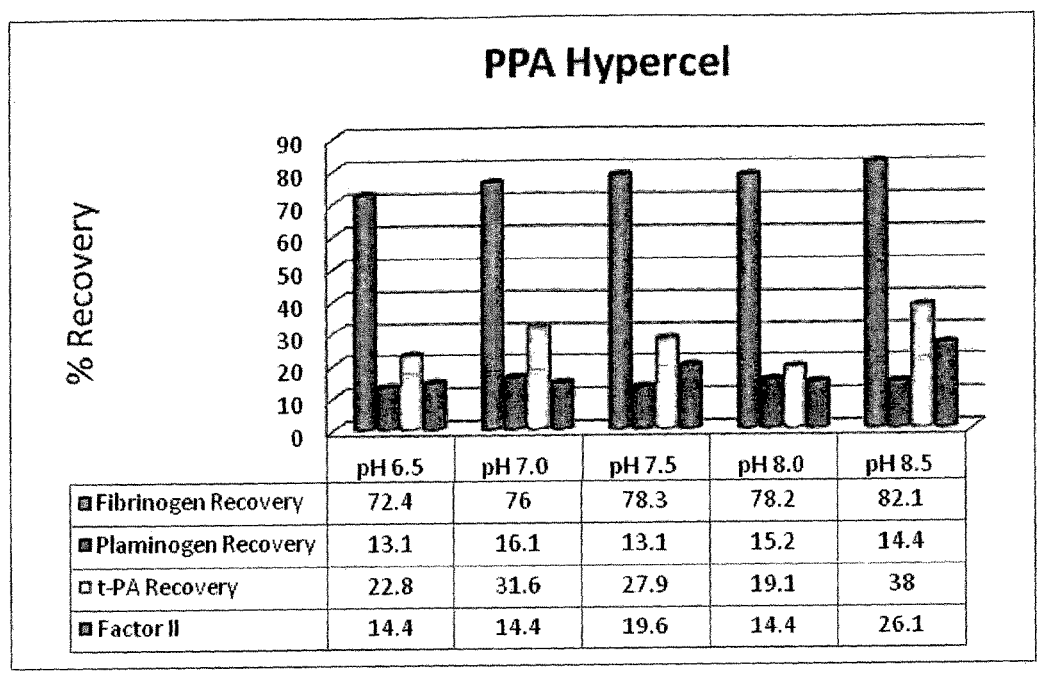
FIG. 2 shows the percentage recovery of fibrinogen, plasminogen, t-PA, and Factor II from a fibrinogen solution over a range of pH levels when the solution is passed through a PPA Hypercel™ in negative mode with respect to fibrinogen. The bars within each group represent (from left to right): Fibrinogen Recovery, Plasminogen Recovery, t-PA Recovery and Factor II.
Figure 3:
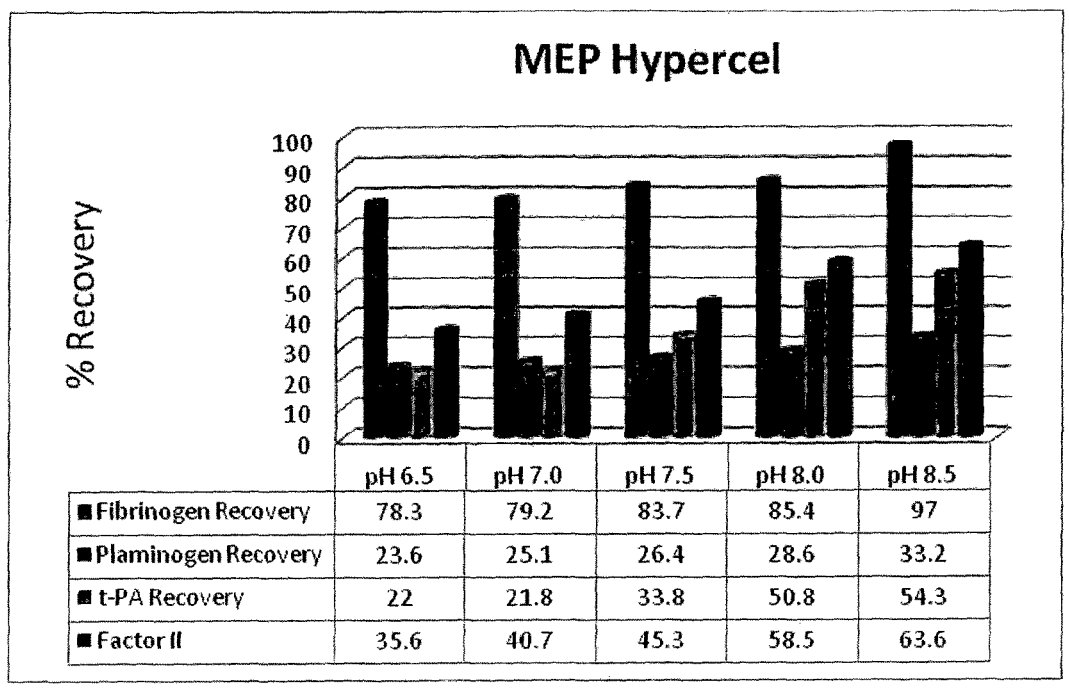
FIG. 3 shows the percentage recovery of fibrinogen, plasminogen, t-PA, and Factor II from a fibrinogen solution over a range of pH levels when the solution is passed through a MEP Hypercel™ in negative mode with respect to fibrinogen. The bars within each group represent (from left to right): Fibrinogen Recovery, Plasminogen Recovery, t-PA Recovery and Factor II.

FIGS. 1 to 3 show step recovery of fibrinogen, plasminogen, t-PA and Factor II post-chromatographic purification using HEA HYPERCEL™, PPA HYPERCEL™ and MEP HYPERCEL™. The results show that pH has little or no effect on plasminogen binding to these resins, whereas the binding of t-PA to the resins appears to be most effective at the lower pH range. The HEA HYPERCEL™ column showed the highest fibrinogen recovery in the drop-through fraction and the operating pH range tested appeared to have little effect on fibrinogen recovery compared to that observed for both PPA and MEP HYPERCEL™ columns. Both PPA and MEP columns displayed highest fibrinogen recovery in the drop-through fraction at pH 8.5.

Example 2—Level of Impurities in a Fibrinogen Solution Reduced Through HEA HYPERCEL™

Figure 4A:
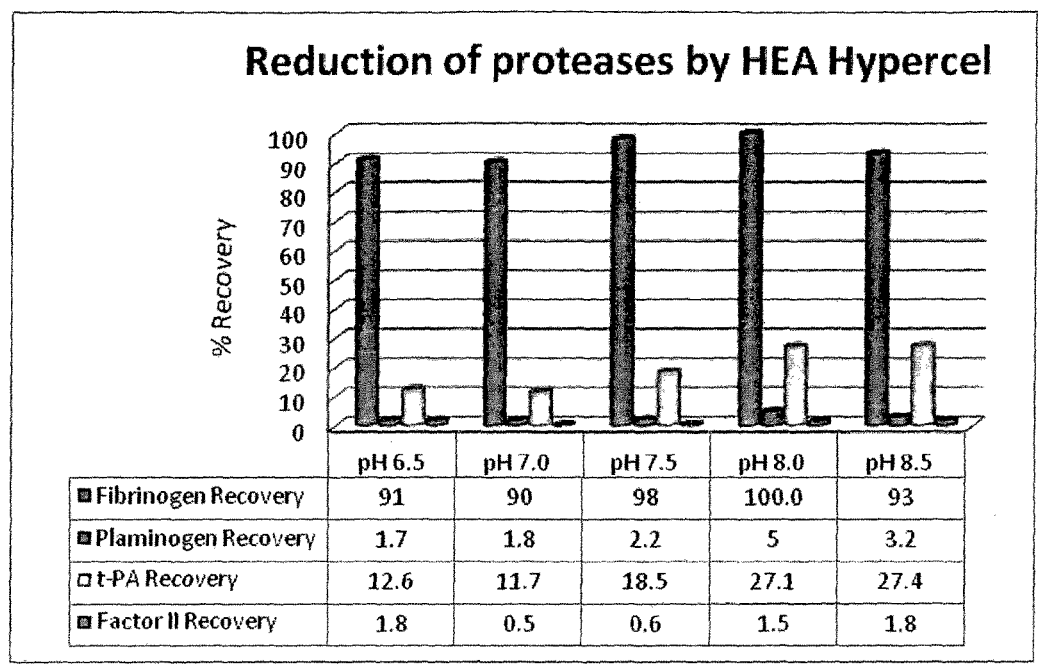
FIG. 4a shows the percentage recovery of fibrinogen, plasminogen, t-PA and Factor II from a fibrinogen-containing solution over a range of pH levels when the solution is passed through a HEA Hypercel™ in negative mode with respect to fibrinogen. The bars within each group represent (from left to right): Fibrinogen Recovery, Plasminogen Recovery, t-PA Recovery and Factor II Recovery.

Approximately 48.5 mL of fibrinogen containing solubilised cryoprecipitate prepared according to Example 1 was applied onto a 5 mL HEA HYPERCEL™ column which was pre-equilibrated in 25 mM Tris at either pH 6.5, 7.0, 7.5, 8.0 or 8.5. HCIC purification was performed in negative mode with respect to fibrinogen, in which fibrinogen was allowed to drop-through in the unbound flow-through fraction, whilst t-PA, plasminogen and Factor 11 remained bound to the resin. FIG. 4a shows step recovery of fibrinogen, plasminogen, t-PA and Factor II during post-chromatographic purification using HEA HYPERCEL™. The results show that pH had little or no effect on the binding of plasminogen and Factor 11 to the HCIC resin, whereas the binding of t-PA to the resin appeared to be most effective at the lower pH range of 6.5-7.0. Recovery of fibrinogen was greater than 90% in the drop-through fraction under different pH conditions despite no column wash being performed. As shown in FIG. 4a, these results demonstrate effective removal of proteases in a crude fibrinogen-containing feed stock, such as solubilized cryoprecipitate, by the HCIC resin. For example, the experimental condition performed at pH 7.0 demonstrated a reduction of ≥99.9% for factor II, 88.3% for t-PA and ≥98.2% for plasminogen from the solubilised cryoprecipitate solution.

Figure 4B:
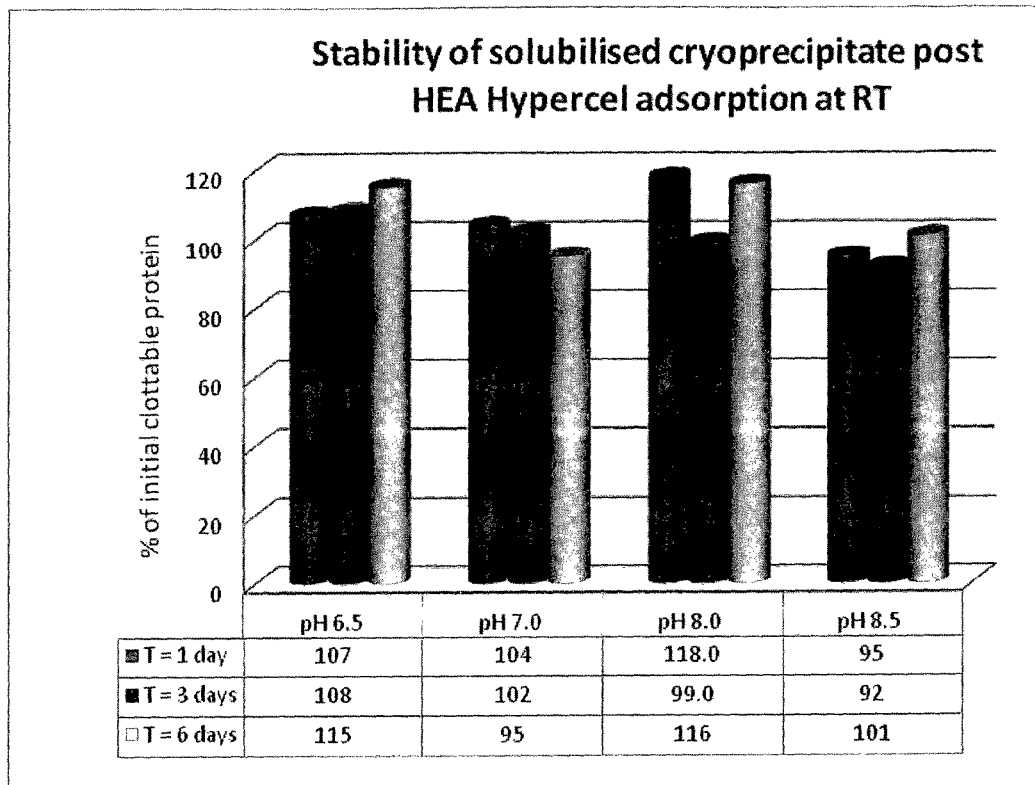
FIG. 4b shows the stability of the fibrinogen containing solution recovered from the drop through fraction of the HEA Hypercel™ column (FIG. 4a) over 6 days at room temperature (approx. 20° C.), as measured by % of initial clottable protein. The bars within each group represent (from left to right): T=1 day, T=3 days, T=6 days.
Figure 4C:
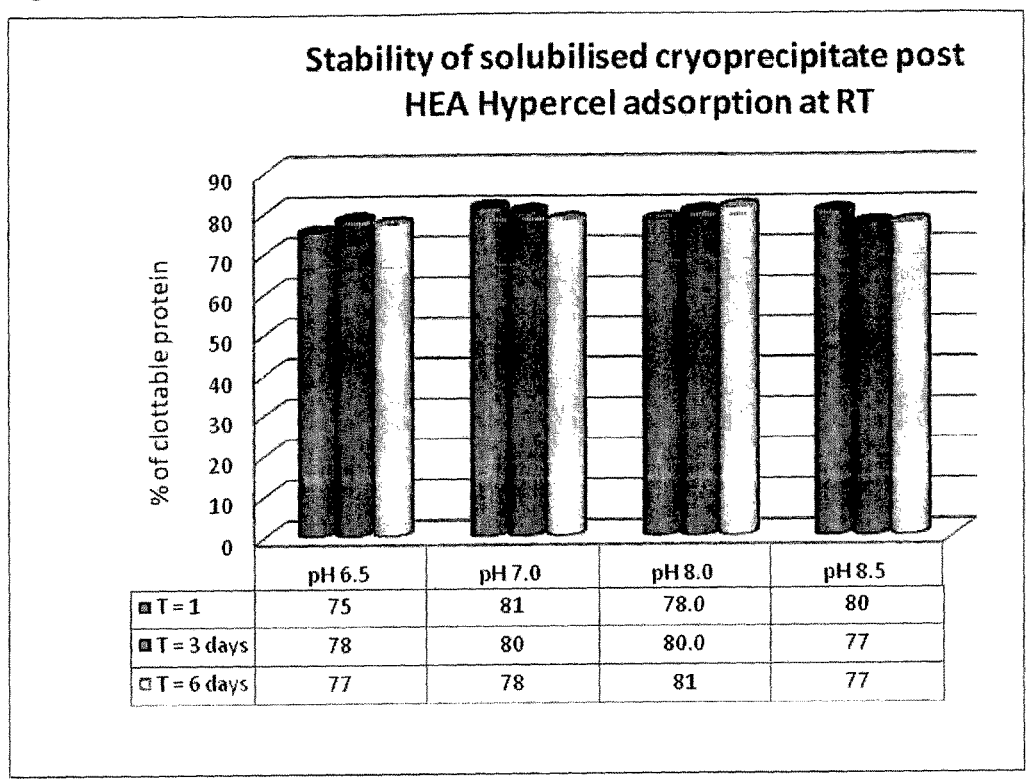
FIG. 4c shows the stability of the fibrinogen containing solution recovered from the drop through fraction of the HEA Hypercel™ column (FIG. 4a) over 6 days at room temperature (approx. 20° C.), as measured by % clottable protein. The bars within each group represent (from left to right): T=1, T=3 days, T=6 days.

The fibrinogen remained stable in solution for at least 6 days at room temperature (approx. 20° C.). The results are presented in FIGS. 4b and 4c.

Example 3—Level of Impurities in a Fibrinogen Solution Purified Through HEA HYPERCEL™

Approximately 500 mL of the fibrinogen-containing supernatant obtained post ALHYDROGEL™ adsorption step generated in accordance with Example 1 was loaded onto an XK 16/30 column packed with 36 mL of HEA HYPERCEL™ resin, pre-equilibrated in 25 mM Tris pH 7.0. The drop-through fraction was collected for fibrinogen, plasminogen, t-PA, and Factor II testing. A summary of the results is provided in Table 1 below.

TABLE 1

| | Volume (mL) | Protein (mg/mL) | Fibrinogen by Clauss (mg/mL) | Plasminogen (ng/mL) | t-PA (pg/mL) | Factor II (U/mL) |
|---|---|---|---|---|---|---|
| Fibrinogen supernatant | 500 | 21.8 | 16.0 | 53172.0 | 1716.5 | 0.00097 |
| Drop-through fraction | 540 | 17.6 | 13.2 | 15655.5 | 706.7 | 0.00025 |
| % recovery in drop- through fraction | | 87.2% | 89.1% | 31.8% | 44.5% | 27.8% |

Example 4—the Effect of Glycine Precipitation on the Level of Impurities in a Fibrinogen Solution Purified Through HEA HYPERCEL™

The fibrinogen-containing supernatant post-ALHYDRO-GEL™ adsorption step generated in accordance with Example 1 was subjected to a further precipitation step by adding a saline solution comprising 2.4M glycine, 2.7M NaCl, 2.1 mM CaCl$^2$ and 23 mM Tri-sodium citrate (pH 6.6-7.3). The solubilised precipitate was warmed to 30° C. before being added to the glycine buffer, which was also incubated to 30° C., at a product to buffer ratio of 1:2. The mixture was allowed to stir for 10 minutes and the resultant precipitate was recovered from the liquid phase by centrifugation. The liquid phase, which contained predominantly fibronectin and IgG, was discarded and the fibrinogen-containing precipitate was collected and resuspended in a solubilisation buffer containing 100 mM NaCl, 1.1 mM CaCl$_2$, 10 mM Trisodium citrate, 10 mM Tris-(hydroxymethyl methylamine) and 4.5 mM sucrose (pH 7.0). The solubilised fibrinogen intermediate (250 mL) was clarified using a 1 μm filter before being passed through an XK 16/30 column packed with 36 mL of HEA HYPERCEL™ resin pre-equilibrated in 25 mM Tris pH 7.0. The drop-through fraction was collected for fibrinogen, plasminogen, t-PA and Factor II testing and a summary of the results is provided in Table 2 below.

The results demonstrate that binding of plasminogen, t-PA and Factor II to the HEA HYPERCEL™ resin was more effective under these processing conditions in comparison to that observed under the conditions described in Example 2. The characterisation results show a step recovery of approximately 93% for fibrinogen, 6% for plasminogen, 12% for t-PA and 5% for Factor II.

Example 5—Preparation of Purified Fibrinogen from Plasma Cryoprecipitate

Process Step 1—solubilisation of plasma cryoprecipitate;

Process Step 2—ALHYDRGEL™ (aluminium hydroxide) adsorption (ALHYDRGEL™ concentration: target 15 to 20% w/w, ranging from 10 to 50% w/w) of solubilised plasma cryoprecipitate and recovery of fibrinogen-containing supernatant using methods such as centrifugation or depth filtration in the presence of a filter aid. Alternatively this step can be replaced with either a HCIC chromatographic step in negative mode (drop through) with respect to fibrinogen or a combination of HCIC and anion exchange chromatography both in negative mode with respect to the fibrinogen. If both HCIC and anion exchange chromatography are used in combination then Process Step 3 is optional;

Process Step 3—glycine precipitation of fibrinogen from the fibrinogen-containing supernatant of Step 2. Alternatively this step can be replaced with an anion exchange chromatography in negative mode with respect to the fibrinogen;

Process Step 4—passing the solubilised glycine precipitate from Step 3 through a HCIC chromatographic resin in negative mode with respect to fibrinogen;

Process Step 5—treating the purified fibrinogen solution recovered in Step 4 with solvent or detergent or pasteurisation to inactivate pathogens;

Process Step 6—passing the treated solution from Step 5 through an anion exchange chromatographic resin in positive mode with respect to fibrinogen, washing the weakly bound proteins from the resin and eluting the fibrinogen from the resin;

Process Step 7—subjecting the fibrinogen eluted from the anion exchange resin in Step 6 to nanofiltration (35 nm or 20 nm or a combination of 35/20 nm); and

TABLE 2

| | Volume (mL) | Protein (mg/mL) | Fibrinogen by Clauss (mg/mL) | Plasminogen (ng/mL) | t-PA (pg/mL) | Factor II (U/mL) |
|---|---|---|---|---|---|---|
| Solubilised fibrinogen intermediate | 250.0 | 29.7 | 30.3 | 48457.0 | 3408.4 | 0.002 |
| Drop-through fraction | 285.2 | 26.4 | 24.6 | 2646.8 | 984.2 | 0.00008 |
| % recovery in drop- through fraction | | 101% | 92.6 | 6.2% | 12.3% | 4.6% |

Process Step 8—subjecting the filtered fibrinogen from Step 7 to ultrafiltration (50, 100, 200 and 300 kDa membrane filters).

Example 6—Preparation of Purified Fibrinogen by Combination of HCIC and Anion Exchange Chromatography Three laboratory scale experiments were completed in which approximately 100 g of cryoprecipitate was prepared according to the steps described in Examples 1 to 3 through to the mixed mode chromatography step using a HEA HYPERCEL™ column.

The drop-through fraction from the HEA HYPERCEL™ column, which contained predominantly fibrinogen, was subjected to an overnight solvent/detergent treatment for virus inactivation.

The virus inactivated solution was then diluted to <10 mS/cm using 25 mM Tris (pH 8.0) prior to being loaded onto an anion exchange column (XK 50/30, GE Healthcare), packed with approximately 412 mL of MACROPREP™-HQ resin that was preequilibrated with 25 mM Tris (pH 8.0). The flow-through fraction was discarded and the MACROPREP™-HQ column washed with 4 column volumes of a washing buffer containing 90 mM NaCl, 50 mM Tris, 20 mM EACA (pH 8.0). Under these chromatographic conditions, the initial flow-through fraction and the wash fractions contain predominantly plasminogen and t-PA, whilst fibrinogen remained bound to the chromatographic resin. The monomeric form of fibrinogen was selectively eluted from the MACROPREP™-HQ column using an elution buffer comprising 200 mM NaCl, 10 mM Tris, 10 mM Tri-sodium citrate, 46 mM sucrose and 1.1 mM $CaCl_2$ (pH 7.0), leaving fibrinogen aggregates and low molecular weight proteins bound to the MACROPREP™-HQ resin.

Figure 5:
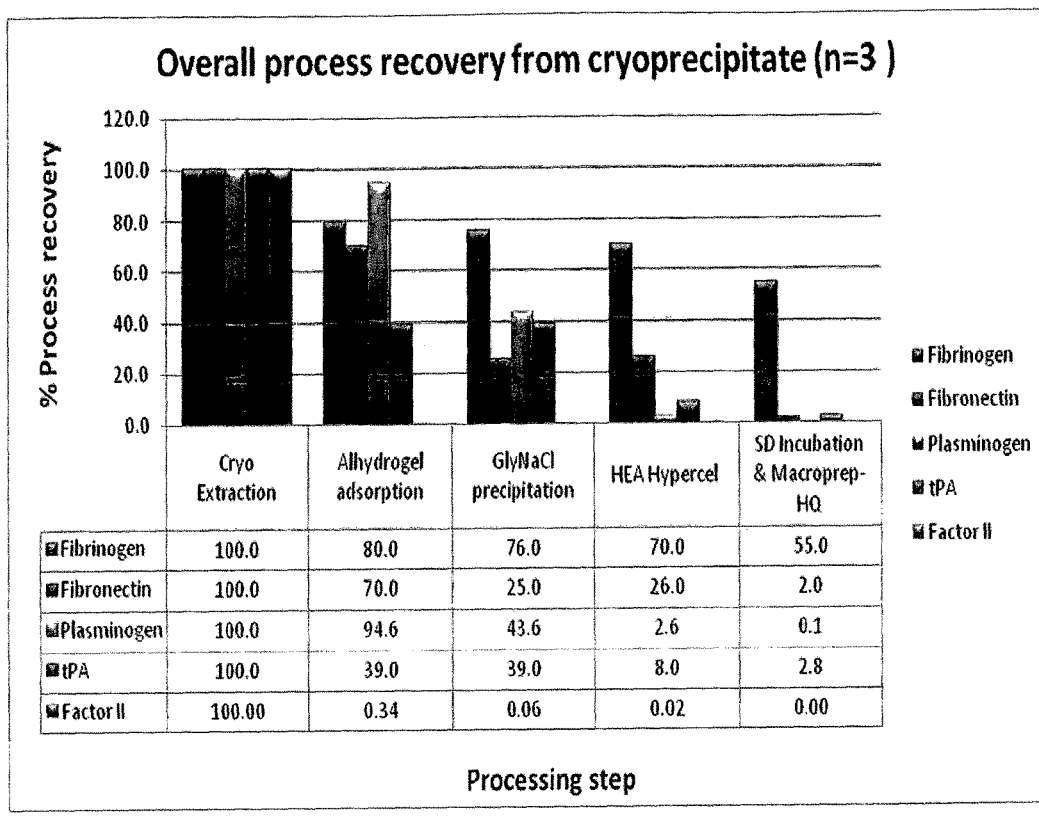
FIG. 5 shows the percentage process recovery for fibrinogen, t-PA, plasminogen and Factor II in fractions derived from a method according to an embodiment of the present invention, from the plasma cryoprecipitate through to the MacroPrep™-HQ eluate. The bars within each group represent (from left to right): Fibrinogen, Fibronectin, Plasminogen, t-PA and Factor II.

Product intermediates generated from solubilised cryoprecipitate through to MACROPREP™-HQ chromatography eluate were characterised for fibrinogen, t-PA, plasminogen, fibronectin and Factor II levels and process step recoveries for each of these proteins at the various process stages. The results are shown in Table 3, which represent a mean value from three separate laboratory scale consistency batches. The overall process recovery for fibrinogen and co-purified proteins starting from the plasma cryoprecipitate through to the MACROPREP™-HQ eluate is shown in FIG. 5.

Figure 6:
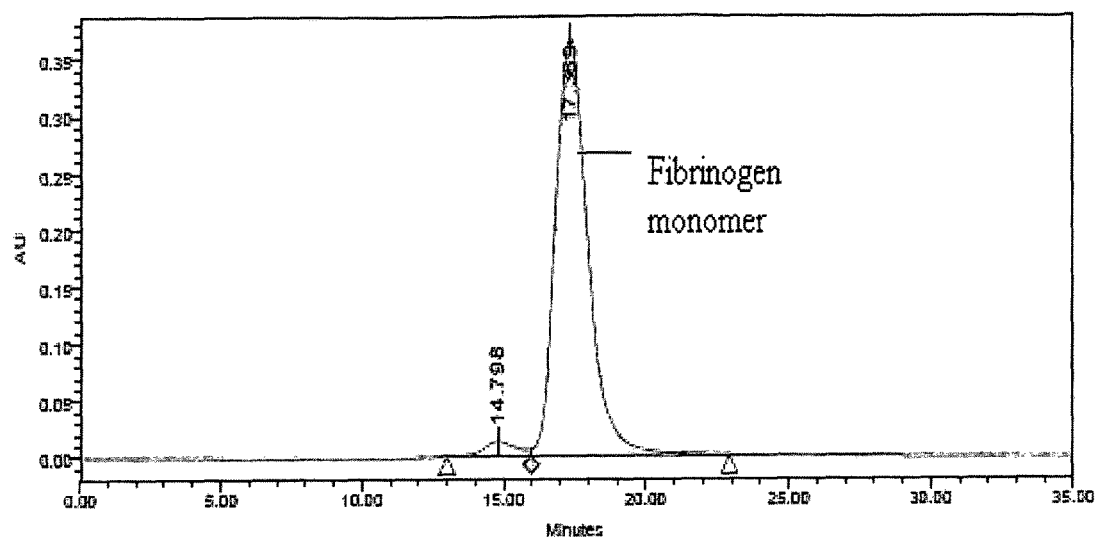
FIG. 6 shows the purity of monomeric fibrinogen that was recovered from the MacroPrep™-HQ chromatographic resin, as measured by analytical size exclusion HPLC chromatogram.

The purity of fibrinogen that was recovered from the MACROPREP™-HQ chromatographic resin was greater than 95%, as revealed by analytical size exclusion HPLC chromatography. A representative of the HPLC profile of fibrinogen analysed on TSKGEL™ G4000SWXL (Tosoh Corporation) is shown in FIG. 6. As shown in FIG. 6, the fibrinogen monomer is eluted at a retention time of approximately 17.4 minutes and contributed to 96.6% of the total peak area, whilst fibrinogen dimer and/or other high molecular weight proteins are eluted at a retention time of approximately 14.8 minutes.

Further fibrinogen batches were manufactured at pilot scale (81 kg plasma equivalent) following the process described in Examples 5 and 6. The characteristics of the fibrinogen preparations are provided in Table 4.

Example 7—Virus Filtration of Purified Fibrinogen

The filterability through a 20 nm virus filter was examined for fibrinogen preparations obtained following method of Example 6 wherein the MACROPREP™-HQ elution step used either 190 mM NaCl (21.5 mS/cm), 200 mM NaCl (22.5 mS/cm), 210 mM NaCl (23.5 mS/cm) or a 200 mM NaCl buffer containing 1% (w/w) arginine (25 mS/cm).

Figure 7:
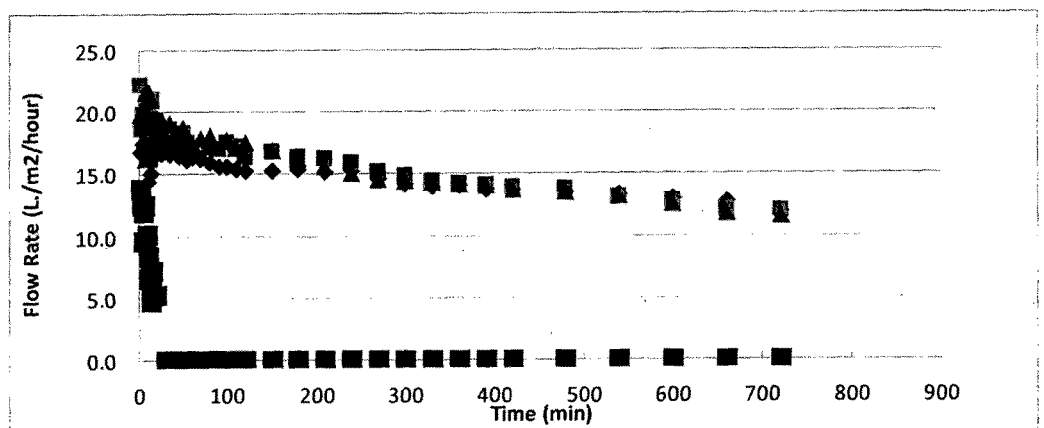
FIG. 7 shows the filterability of fibrinogen recovered from the MacroPrep™-HQ chromatographic resin using elution buffers with different conductivities (190 mM NaCl, 21.5 mS/cm (diamonds); 200 mM NaCl, 22.5 mS/cm (squares); 210 mM NaCl, 23.5 mS/cm (triangles); 1% (w/w) arginine/ 200 mM NaCl, 25 mS/cm (cross)).

The method involved formulating the preparations with 3% (w/w) arginine at a pH of about 7.5 (the protein concentration of the samples was approximately 6 g/L). The formulated preparations were then filtered using 0.1 μm filter prior to the virus filtration step. The virus filtration step was carried out using a 47 mm Pall SV4™ filter in dead-end mode using a constant pressure of 1.8 bar. Results indicate that fibrinogen preparations obtained from the MACROPREP™ HQ column using either the 190 mM, 200 mM or 210 mM resulted in similar filtration characteristics. In contrast, the fibrinogen preparation eluted from the MACROPREP™ HQ column using 200 mM NaCl buffer containing 1% (w/w) arginine rapidly fouled the filter (FIG. 7).

Example 8—Stability Study

Figure 8:
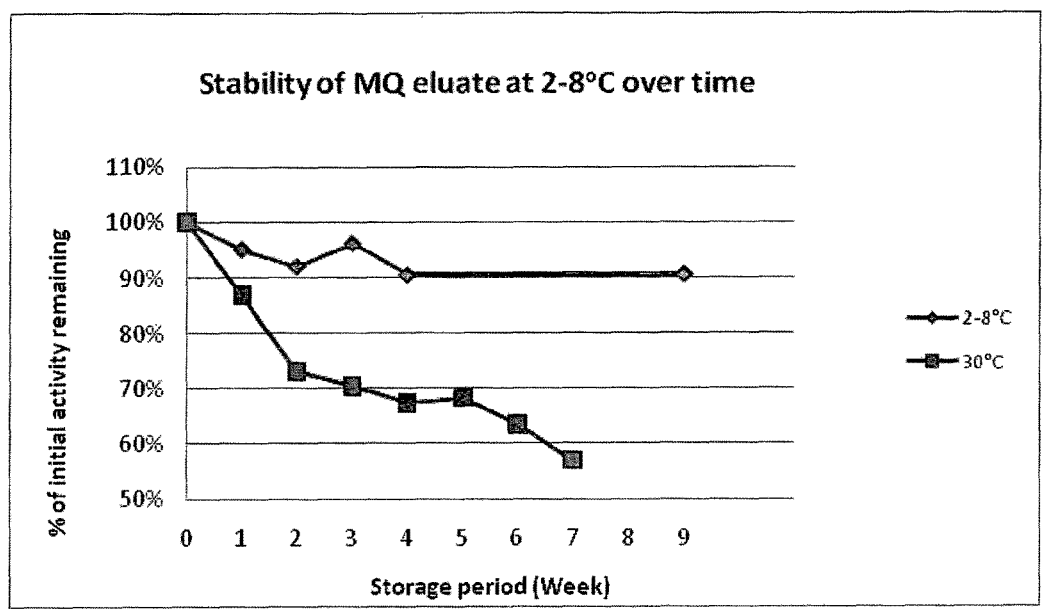
FIG. 8 shows the fibrinogen activity as a percentage of the initial fibrinogen activity at t=0 of liquid fibrinogen recovered from the MacroPrep™-HQ chromatographic resin that is stored at either 2-8° C. (diamonds) for a 9 week period or 30° C. (squares) for a 7 week period.

Purified fibrinogen solution recovered by the method described in Example 5 above was sterile filtered and subjected to a stability study over a 9/7 week period at 2°-8° C. or 30° C. The liquid fibrinogen preparation placed at 2°-8° C. retained from about 90% of its original activity as measured by the Clauss method after the 9 week storage period. The liquid fibrinogen preparation placed at 30° C. retained about 70% of its original activity after the 2 week storage period and did not lose further activity for at least 5 weeks. A further reduction in activity to below 60% was observed by week 7 of incubation at 30° C. The loss of fibrinogen activity at 30° C. is likely to be attributed to heat denaturation, rather than proteolytic degradation, as the addition of a protease inhibitor (C1 Esterase) did not inhibit the loss of fibrinogen activity over the 5 week storage period. A summary of the stability data is provided in FIG. 8.

TABLE 3

| Processing steps | Protein mg/mL (n = 3) | | Clottable protein (n = 3) | | Plasminogen (n = 3) | | t-PA (n = 3) | | Factor II (n = 3) | | Fibronectin (n = 3) | |
|---|---|---|---|---|---|---|---|---|---|---|---|---|
| | Conc. (mg/mL) | Step recovery (%) | Conc. (mg/mL) | Step recovery (%) | Conc. (ug/mL) | Step recovery (%) | Conc (ng/mL) | Step recovery (%) | Conc. (U/mL) | Step recovery (%) | Conc (mg/mL) | Step recovery (%) |
| Solubilised cryoprecipitate | 31.0 | | 23.5 | | 65.44 | | 9.00 | | 0.28041 | | 8.15 | |
| Solubilised cryoprecipitate filtrate- post Al(OH)3 treatment | 15.8 | 81% | 11.6 | 80% | 39.04 | 96% | 2.20 | 39% | 0.00057 | 0.3% | 3.47 | 70% |

TABLE 3-continued

| Processing steps | Protein mg/mL) (n = 3) | | Clottable protein (n = 3) | | Plasminogen (n = 3) | | t-PA (n = 3) | | Factor II (n = 3) | | Fibronectin (n = 3) | |
|---|---|---|---|---|---|---|---|---|---|---|---|---|
| | Conc. (mg/mL) | Step recovery (%) | Conc. (mg/mL) | Step recovery (%) | Conc. (ug/mL) | Step recovery (%) | Conc (ng/mL) | Step recovery (%) | Conc. (U/mL) | Step recovery (%) | Conc (mg/mL) | Step recovery (%) |
| Solubilised glycine saline precipitate | 30.3 | 76% | 27.6 | 95% | 45.78 | 46% | 5.55 | 101% | 0.00025 | 26.0% | 3.18 | 37% |
| HEA Hypercel drop-through fraction | 22.7 | 93% | 20.5 | 92% | 2.20 | 6% | 0.98 | 22% | 0.00008 | 39% | 2.79 | 97% |
| SD Incubation & Macroprep-HQ chromatography | 7.4 | 80% | 6.7 | 79% | 0.04 | 5% | 0.13 | 38% | <0.00002 | 0% | 0.09 | 8% |

TABLE 4

| Batch No. | 1 | 2 | 3 | 4 |
|---|---|---|---|---|
| % Clottable protein | 96 | 94 | 95 | 94 |
| tPA per mg protein (pg/mg) | 12 | 24 | 17 | 21 |
| Plasminogen per mg protein (ng/mg) | 5 | 6 | 5 | 6 |
| Factor II per mg protein (IU/mg) | $3.3 \times 10^{-7}$ | $3.9 \times 10^{-7}$ | $5.5 \times 10^{-7}$ | $9.6 \times 10^{-7}$ |

TABLE 5

| | Volume (mL) | Factor VIII (IU/mL) | VWF:RCo (IU/mL) | Plasminogen (ng/mL) | t-PA (pg/mL) |
|---|---|---|---|---|---|
| Pre HEA Hypercel | 3377.7 | 10.9 | 11.9 | 28617.1 | 2957.4 |
| Post HEA Hypercel Drop-through fraction | 3949.3 | 8.7 | 10.6 | 1874.0 | 683.5 |
| % recovery in drop-through fraction | | 93% | 104% | 8% | 27% |

Example 9—Reduction of Plasma Protease Levels in a Factor VIII and/or VWF Containing Solution Using HEA Hypercel This example demonstrates that the HCIC chromatography step can also be employed to reduce proteases in Factor VIII and for VWF containing preparations. The method involved clarifying the fibrinogen containing solution obtained from Example 4 using a depth filter before then passing the clarified solution through a second hydrophobic charge induction chromatographic (HCIC) resin. The HCIC step was operated under conditions to allow proteases such as plasminogen to bind to the resin whilst Factor VIII and VWF were able to pass through the resin. In particular an XK 50/30 column was packed with 340 mL of HEA Hypercel™ resin. The column was pre-equilibrated in 50 mM Tris pH 6.7. The clarified fibrinogen solution prepared according to Example 4 was then loaded onto the column and the column washed with 50 mM Tris pH 6.7. The drop-through fraction was collected and the levels of Factor VIII, VWF, plasminogen and t-PA determined (VWF:RCo=Von Willebrand Ristocetin Cofactor). A summary of the average results obtained from 4 individual runs is provided in Table 5. The results indicate that the HCIC chromatographic step effectively removed proteases such as plasminogen and tPA from the fraction comprising the Factor VIII and VWF. In addition good recoveries of Factor VIII and VWF were observed.

Example 10—Comparative Study of Fibrinogen Purified from Different Methods

The fibrinogen preparation manufactured according the method of the present invention, as described in Example 6, was compared to fibrinogen preparations manufactured by methods described in WO2001048016, WO2012038410 and WO2013135684.
(a) Fibrinogen preparation manufactured by a preferred embodiment of the methods described in WO2001048016.
Briefly the method involved suspending Fraction I paste in Extraction buffer (0.8M NaCl, 5 mM EACA (epsilon-aminocaproic acid), 20 mM Na-citrate, 60 IU/mL heparin, pH 7.3) (1 g of Fraction I to 8.33 g Extraction buffer). The solution was then mixed at 37° C. for 1.5 hours prior to 50 g of a 2% Al(OH)$_3$ (ALHYDROGEL™) solution being added per gram of Fraction I (10.8%). The mixture was stirred for 15 minutes at room temperature and then centrifuged at 5000 g for 10 minutes with the pellet discarded. To the ALHYDROGEL™-treated supernatant was added a glycine/NaCl buffer (2.1M glycine, 20 mM Na-citrate, 3.6M NaCl and 2.4 mM CaCl$_2$) (both solutions were pre-equilibrated to 30° C.). The addition of the supernatant to the buffer was completed in about 4.5 minutes (1 part supernatant to 2.05 parts buffer). The mixture was then stirred for 20 minutes at 30° C. prior to being centrifuged for 10 minutes at 5010 g (the supernatant was discarded). The precipitate was then resolubilized in buffer D (100 mM NaCl, 11.1 mM CaCl$_2$, 10 mM Na-citrate, 10 mM tris, 45 mM sucrose, pH 6.9) at room temperature with mixing for 2 hours (⅓ the volume of that used to resuspend fraction I) (Example 1, sections 1.1.1-1.1.6, WO0148016). The resolublized fibrinogen containing solution was then loaded onto a MACROPREP™ HQ column (XK26 with bed height 20 cm). The column was preequilibrated with at least 1.5 column volumes (CV) of MQ buffer (50 mM Tris, 100 mM NaCl, 20 mM EACA, pH 8.0 at 10 mL/min (113 cm/hr). The equilibration was continued until the conductivity post column was 90-110% of the prepared buffer. The fibrinogen solution was then loaded onto the column and the column washed with 6 CV of MQ buffer. The fibrinogen was eluted as a single peak using ME buffer (500 mM NaCl, 1.1 mM $CaCl_2$, 10 mM Na-citrate, 10 mM Tris and 45 mM sucrose, pH 7.0). The column can be regenerated using 2CV 1M NaCl (Example 2, WO2001048016).

Cryoprecipitate, produced from plasma by established methods, was reconstituted or solubilised at about neutral pH, subjected to adsorption with $Al(OH)_3$ and the resulting gel removed by centrifugation. The supernatant was then virus inactivated by solvent/detergent (S/D) treatment. SID compounds, Triton and TnBP were extracted with vegetable oil and the water-phase was contacted with FRACTOGEL® EMD-TMAE. Chromatographic conditions (pH-value of 6.9-7.1 and an osmolality of 570-610 mosmol/l) were employed under which the fibrinogen did not bind to the gel and hence was found in the flow-through or supernatant. The solution of unbound fibrinogen was stirred for about 90 minutes after addition of glycine (1 mol/l final concentration and pH=7.4) in the presence of 20 mM EDTA to precipitate fibrinogen. The fibrinogen containing precipitate was then separated by centrifugation, yielding an intermediate fibrinogen paste. The intermediate fibrinogen paste was re-suspended in 20 mM Tris buffer (pH=about 8.0). The suspension obtained was then filtered and subjected to ultra/diafiltration. The resulting fibrinogen containing solution was then loaded onto GIGACAP™ Q-650M® and the chromatographic gel or resin was pre-equilibrated with the same Tris buffer as used for resuspension before applying the fibrinogen solution. Loosely bound substances were washed out with the equilibration buffer followed by washing with a wash buffer (1.5 g/l sodium citrate, 6.0 g/l sodium chloride, adjusted to about pH=7.0 and a conductivity of about 12.0 mS/cm). Fibrinogen was then eluted from the chromatographic column with an elution buffer (1.5 g/l sodium citrate, and 10.0 g/l glycine adjusted to the same pH as the washing buffer and adjusted with about 7.0 g/l NaCl to the conductivity of 13.1-15 mS/cm.).

The fibrinogen containing solutions obtained from the methods described in WO02001048016, WO2012038410 and WO2013135684 were tested for total protein (Biuret), fibronectin and plasminogen levels. In addition, samples were placed on stability trial at 2-8° C. and 30° C.

A comparison of the properties of the fibrinogen preparations is provided in Table 6. The results of the study indicate that fibrinogen manufactured from the methods of the present invention contain lower levels of plasminogen compared to the other methods.

TABLE 6

| Fibrinogen preparations | Method of Example 6 | Method of WO2001048016 | Method of WO2012038410/ WO2013135684 |
|---|---|---|---|
| Fibronectin (µg/mg protein) | 12 | 11 | 0.09 |
| Plasminogen (ng/mg protein)) | 5 | 54 | 791 |

The invention claimed is:

1. A pharmaceutical formulation comprising a solution of fibrinogen and an effective amount of a stabilizer, wherein the fibrinogen is recovered by the method of:
   (i) passing a feedstock comprising fibrinogen through a hydrophobic charge-induction chromatographic resin equilibrated at a pH from 6.5 to 8.5, wherein at least one protein selected from the group consisting of plasminogen, tissue plasminogen activator, and other protease(s) present in the feedstock binds to the resin; and
   (ii) recovering a solution comprising at least 80% total protein of fibrinogen which passes through the resin, wherein the concentration of tissue plasminogen activator is less than 50 pg/mg and the concentration of plasminogen is less than 1 µg/mg in the recovered fibrinogen solution.

2. The pharmaceutical formulation of claim 1, wherein the recovered solution comprises at least 80% total protein of monomeric fibrinogen.

3. The pharmaceutical formulation of claim 1, wherein the fibrinogen retains from about 90% to 100% activity after at least 4 weeks in storage of the solution at a temperature of about 0° C. to about 8° C.

4. The pharmaceutical formulation of claim 1, wherein the fibrinogen retains from about 60% to about 70% activity after 5 weeks in storage of the solution at a temperature of about 30° C.

5. The pharmaceutical formulation of claim 1, further comprising a pharmaceutically acceptable carrier.

6. The pharmaceutical formulation of claim 5 having a volume of at least 5 mL and comprising at least 5 mg/mL fibrinogen.

7. The pharmaceutical formulation of claim 5 having a volume of at least 5 mL and comprising at least 20 mg/mL fibrinogen.

8. A method of treating or preventing a condition associated with fibrinogen deficiency, the method comprising administering to a subject in need thereof the pharmaceutical formulation of claim 1.

9. The method of claim 8, wherein the condition is selected from the group consisting of afibrinogenemia, hypofibrinogenemia and dysfibrinogenemia.

10. A fibrin glue comprising a solution of fibrinogen, wherein the fibrinogen is recovered by the method of:
   (i) passing a feedstock comprising fibrinogen through a hydrophobic charge-induction chromatographic resin equilibrated at a pH from 6.5 to 8.5, wherein at least one protein selected from the group consisting of plasminogen, tissue plasminogen activator, and other protease(s) present in the feedstock binds to the resin; and
   (ii) recovering a solution comprising at least 80% total protein of fibrinogen which passes through the resin, wherein the concentration of tissue plasminogen activator is less than 50 pg/mg and the concentration of plasminogen is less than 1 µg/mg in the recovered fibrinogen solution.

* * * * *